(12) United States Patent
Dong et al.

(10) Patent No.: US 11,913,933 B1
(45) Date of Patent: Feb. 27, 2024

(54) MINIATURE SENSORS WITH PROBE INSERTABLE INTO AND FOR OBTAINING MEASUREMENTS FROM PLANTS AND A VARIETY OF OTHER MEDIUMS

(71) Applicant: Iowa State University Research Foundation, Inc., Ames, IA (US)

(72) Inventors: Liang Dong, Ames, IA (US); Md. Azahar Ali, Ames, IA (US); Xinran Wang, Ames, IA (US); Michael Castellano, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 354 days.

(21) Appl. No.: 17/247,857

(22) Filed: Dec. 28, 2020

Related U.S. Application Data

(62) Division of application No. 15/994,572, filed on May 31, 2018, now Pat. No. 10,921,303.
(Continued)

(51) Int. Cl.
*G01N 33/00* (2006.01)
*A01C 1/00* (2006.01)
(Continued)

(52) U.S. Cl.
CPC ........... *G01N 33/0098* (2013.01); *A01C 1/00* (2013.01); *G01N 27/4145* (2013.01)

(58) Field of Classification Search
CPC ... G01N 33/0098; G01N 27/4145; A01C 1/00
(Continued)

(56) References Cited

U.S. PATENT DOCUMENTS 2,689,141 A 9/1954 Kiekhaefer
4,020,830 A 5/1977 Johnson et al.
(Continued)

FOREIGN PATENT DOCUMENTS

JP 6273434 A 9/1994
JP 2008233047 A 10/2008
(Continued)

OTHER PUBLICATIONS

Britz et al., "Smart Nitratre-Selective Electrochemical Sensors With Electrospun Nanofibers Modified Microelectrode", 2014 IEEE Int'l Conf. on Systems, Man, and Cybernetics, 4 pages, Oct. 5, 2014.
(Continued)

*Primary Examiner* — Christine T Mui
(74) *Attorney, Agent, or Firm* — McKee, Voorhees & Sease, PLC

(57) ABSTRACT

Apparatus, methods, and systems for transducing measurements from medium of interest. One non-limiting example is in planta monitoring of plants. In one aspect, a micro- or nano-scale probe body includes one or more microprobes (e.g. microneedles or waveguides) to access desired plant tissue, and one or more microsensors on the probe body. A microcircuit on or in the probe body transduces relevant measurements from the microsensor(s). An output interface allows storage, communication, or transfer of the transduced measurement for further use. Non-limiting examples are processing into estimations of chemical concentrations or the like for biochemical sensing. As such, if used as in planta sensors, they can be minimally invasive and cost effective for both single use and use in sets for plural plants with one central station.

32 Claims, 28 Drawing Sheets

Related U.S. Application Data

(60) Provisional application No. 62/513,307, filed on May 31, 2017.

(51) Int. Cl.
  *G01N 27/414* (2006.01)
  *G01N 27/41* (2006.01)

(58) Field of Classification Search
  USPC .......................................................... 436/110
  See application file for complete search history.

(56) References Cited

U.S. PATENT DOCUMENTS

| | | |
|---|---|---|
| 5,627,922 A | 5/1997 | Kopelman et al. |
| 6,303,386 B2 | 10/2001 | Klimant et al. |
| 6,306,594 B1 | 10/2001 | Cozzette et al. |
| 6,790,599 B1 | 9/2004 | Madou |
| 6,889,165 B2 | 5/2005 | Lind et al. |
| 7,226,442 B2 | 6/2007 | Sheppard, Jr. et al. |
| 7,797,367 B1 | 9/2010 | Gelvin et al. |
| 7,830,228 B2 | 11/2010 | Brown et al. |
| 8,115,448 B2 | 2/2012 | John |
| 9,291,284 B2 | 3/2016 | Penterman et al. |
| 2002/0138049 A1 | 9/2002 | Allen et al. |
| 2003/0209451 A1 | 11/2003 | Dineen et al. |
| 2004/0029213 A1 | 2/2004 | Callahan et al. |
| 2006/0046375 A1 | 3/2006 | Chou et al. |
| 2007/0194913 A1 | 8/2007 | Yokoshima et al. |
| 2008/0014897 A1 | 1/2008 | Cook et al. |
| 2017/0010296 A1 | 1/2017 | Shimokawa et al. |
| 2017/0030877 A1 | 2/2017 | Miresmailli et al. |
| 2017/0234820 A1 | 8/2017 | Lettow |

FOREIGN PATENT DOCUMENTS

| | | |
|---|---|---|
| JP | 2014211407 A | 11/2014 |
| WO | 2015166493 A2 | 11/2015 |

OTHER PUBLICATIONS

Washita et al., "Needle-Type In-Situ Plant Water Content Sensors with Polyethersulfone Membrance", Transducers, Appendix E1, 4 pages, Jun. 21, 2009.

Ober et al., "A microsensor for direct measurement of O2 partial pressure within plant tissues", Journal of Experimental Botany, vol. 47, No. 296, pp. 447-454, Mar. 1996.

Nagasawa Masahi, JP 2008-233047 English Translation, dated Oct. 2, 2018, pp. 1-25 obtained on May 18, 2020.

Sugata Kazuhiro, JP 6-273434 English Translation, dated Sep. 30, 1994, pp. 1-11, obtained on May 18, 2020.

MINIATURE SENSORS WITH PROBE INSERTABLE INTO AND FOR OBTAINING MEASUREMENTS FROM PLANTS AND A VARIETY OF OTHER MEDIUMS

CROSS-REFERENCE TO RELATED APPLICATIONS

This is a Divisional application of U.S. Ser. No. 15/994,572 filed on May 31, 2018, which claims the benefit of Provisional Application U.S. Ser. No. 62/513,307 filed on May 31, 2017, both of which are incorporated herein by reference in their entirety.

GOVERNMENT RIGHTS

This invention was made with Government support under Grant No. DE-AR0000824, awarded by the United States Department of Energy, and Grant No. 2017-67013-26463 awarded by the United States Department of Agriculture/National Institute of Food and Agriculture. The Government has certain rights in this invention.

I. BACKGROUND OF THE INVENTION

A. Field of the Invention

The present invention relates to sensing a variety of mediums by use of small and even miniature-sized sensor assemblies which can both obtain a measurement of the medium, or relate it to the medium, and store, convert, or communicate the measurement. In particular, the miniature sensors are configured with a probe that is insertable into the medium, but also carry on-board or use off-board electrical circuitry to facilitate the taking of a measurement. The miniature size and ability to probe the medium, most times nondestructively or minimally invasive, allows in situ sensing. In one non-limiting example, such sensors can be adapted for real-time, in planta (including in vivo) sensing of tissue such as plants for biological, chemical and physical parameters. Other mediums include but are not necessarily limited to soil, liquids including water, animal feces or manure, and even individual cells.

B. Problems in the State of the Art

A traditional technique for testing or measuring tissue is in vitro. A sample of the tissue is extracted and taken to a laboratory setting. The controlled conditions in the laboratory promote repeatability and accuracy of testing. However, this is destructive of the tissue and can be quite invasive of the host of the tissue. The samples must be transported, sometimes long distances, to the lab.

Furthermore, in vitro testing may produce different results than in vivo testing. An increasing body of science indicates this. Separation of the sample from the host may miss out on important interactions. Also, in vitro sampling correlates the sample to one point in time in the tissue development. There can be great value in repeated in vivo measurements over time for continuous or semi-continuous monitoring.

However, the ability to sample or measure in vivo tissue provides significant challenges. The process must not materially disrupt the natural processes and development of the host or the tissue. For example, the measuring components cannot be too large, heavy, or invasive/destructive. They must be practical from an economic standpoint. It can be beneficial to monitor a plurality of hosts from a population to get a better picture of how certain processes vary over a population. In the example of plants, it is difficult if not impractical to sample every plant in a field. Typically, no more than a few plants are sampled and extrapolations made about the whole population. But there can be significant variations between plants across a field. Soil type, moisture level, nutrient availability, temperature and other factors can result in significant variations between plants across a field. It could be very valuable to be able to monitor the same or different plant parameters across the field. Again, however, this implicates cost, complexity, and overhead. It also implicates issues with how sensors at individual plants can be installed, operated, and monitored in planta including in vivo, and including over variable periods of time, environmental conditions, and plant growth stages. One example is monitoring a plant nutrient such as nitrogen.

It can not only be of interest to monitor over time plural plants of a population, but sometimes different locations of a single plant. For example, monitoring nitrogen uptake at root, stalk, and shoots of the same plant may lead to discoveries of that plant's processes not possible if monitoring a single location on the plant. This, again, however implicates cost, complexity, practicality and the ability of a single plant to support plural sensors.

The ability to precisely measure N uptake of plants would allow farmers to better manage fertilizer application. Crop plants are the end user of fertiliser (N, P, K, etc.). Unfortunately, current laboratory-based tools to measure the N amount in planta are often destructive, time-intensive, and costly. For example, corn stalk nitrate concentration is often measured only once post-senescence. Alternative sensing methods that rely on optical properties of plants suffer from chlorophyll saturation, atmospheric and soil interference, bulkiness, and high cost. Efficient monitoring of in planta nutrient uptake is not yet possible. Our plant sensor technology has been for the first time enabled in-plant nitrate measurements.

Similar issues exist with sensing other nutrients, phenotypes, characteristics, or processes in plants. For example, the ability to monitor in real time in planta any number of things could be very valuable.

While sensor technology is advancing rapidly, applying it to plants presents a variety of competing, and sometimes antagonistic, issues for the designer. Consider the following issues.

Ideally the sensing would be minimally invasive and non-destructive. Interference with normal plant growth and processes ideally would be avoided, especially if the probe or implantable is left in place for extended periods of time. However, this indicates the probe or implantable must be minute which presents huge challenges regarding including in the probe the necessary functional components for sensing. Typically, this includes the need for electrical power at the sensing site.

Accuracy of sensing requires good access to the plant tissue and constituents of interest. However, this presents a number of challenges. If the sensing is implantable or insertable in planta (including in vivo), it is difficult to confirm accurate placement at the tissue or constituents of interest. Even if placement can be confirmed, over time there is uncertainty whether the sensor will continue to have the correct access or placement in a growing plant. Furthermore, if the sensor is made at very small scales (e.g. micro), it is challenging to assure that it will access the intended tissue or constituents to the exclusion of other tissue or constituents.

It can also be beneficial to be able to use such sensors in multiple positions in a plant or in multiple plants. But this runs into the problem of cost. This also raises the issues of complexity and access to the sensors and their measurements. Challenges include how plural small sensors can communicate their measurements; how to effectively and efficiently access many sensors at different plant positions or in different plants; and how electrical power can be provided to the sensors for both sensing functions and data output. At minute form factors, these challenges are difficult.

It would also be beneficial to take sensor measurements at any time and multiple times, including periodically over relatively long spans of time. Competing interests involve how the sensors can be maintained in operating condition and respond to such demands in a manner which is labor and cost effective.

Further difficulties can arise in the sense of robustness for at least the typical range of environmental conditions related to plant growth and development. That environment can present a wide range of temperatures, moisture levels, debris, and atmospheric conditions.

Therefore, allowing the goal of real-time, in planta (including in vivo) monitoring is attractive, the ability to do so in a practical way is neither straight-forward or predictable. The competing factors at work do not allow this. Some of those factors include how to access relevant plant tissues, how to transduce relevant measurements from the accessed plant tissue, and how to capture the transduced measurements for further use. These must be balanced with cost, size, accuracy, reliability issues. Furthermore, the ability to provide electrical power to sensors and communication data from them add further complexities. All of these are in the context of having reliable mechanical installation to the plant, including over substantial periods of time and through substantial variations in environmental conditions.

Similar or analogous issues exist regarding mediums other than plant tissue. For example, the ability to probe and take measurements of soil, water, or other mixtures or fluids may benefit from miniature, relatively inexpensive, substantially self-contained sensors. Similar to in planta sensors, soil sensors could monitor nutrient levels, water levels, and other biochemical constituents for purposes of evaluating soil makeup, agronomic variables, or agricultural practices. Similarly, small relatively low-cost sensors inserted into water (e.g., tile water and overland runoff from crop areas) could measure constituents related to environmental factors, agronomic factors, and toxins, just to name a few. Also, the ability to probe, sense, and/or monitor either one parameter, or plural parameters, economically, unobtrusively, and efficiently at the location of the medium of interest could provide much value. The same is true of the ability to quantify one or more of a variety of parameters (e.g. chemical, biological, etc.) in a variety of mediums of interest (e.g. plants, animals, fluids, soil, cells, etc.).

Still further, other mediums whether or not related to agriculture, can benefit similarly. One example would be animal feces or manure. Relatively small and low-cost sensors could provide on-site, rather than requiring laboratory testing, related to animal husbandry factors, animal health, or environmental conditions.

Still further, small sensors with small probe elements could even be used to interrogate or probe similar scale mediums such as animal or human cells. A sufficiently small probe inserted into a cell could provide at least in situ an immediate feedback of measurements. In some cases, if the probe is sufficiently small and configured appropriately, it can be a nondestructive interrogation. Techniques such as microscopy could be used to help insertion of the probe into the right cell.

II. SUMMARY OF THE INVENTION

A. Objects, Features, and Advantages of the Invention

It is therefore a principle object, feature, aspect, or advantage of the present invention to provide sensors, methods, and systems which improve over or solve problems and deficiencies in the present state of the art.

Other objects, features, aspects, and advantages of the present invention include provision of apparatus, methods, or systems for sensors that have at least miniature or micro-scale probe elements that:

a. are minimally invasive of the medium being investigated, including but not limited to plant growth and development;

b. provide reliable access to and sampling of the desired or relevant medium, including but not limited to plant tissue;

c. promote reliable and accurate transduction of relevant measurements from the relevant medium or its constituents with good measurement accuracy;

d. provide effective ways to capture the measurements for storage, communication, or transfer for further use;

e. are cost effective;

f. are operationally practical, including for plural sensors per medium being investigated or sensors in plural mediums being investigated;

g. are capable of reliable insertion into a medium, including mounting to plants and withstanding typical environmental conditions for growing plants or emplacing into a medium (e.g. soil or other particulates, water or other fluids, animal waste, living cells, or other);

h. are energy consumption efficient and effective;

i. are adaptable to a variety of conditions and applications;

j. can be manufactured in efficient and cost-effective ways;

k. provide needed or improved precision and accuracy of measurements;

l. can be used with systems and methods that utilize the sensor monitoring in a variety of ways; and/or m. allow real-time, at least in situ, single or plural measurements or monitoring over a range of measuring periods.

B. Aspects of the Invention

1) In general, the invention relates to methods, apparatus, and systems to access to relevant medium with one or more probe elements. Whether solid in cross-section or hollow, the probe element has a form factor to be inserted into and access relevant medium. In the case of plant tissue, the probe can be a microneedle form factor designed to be inserted into the plant (e.g. into the xylem).

2) Transduce one or more relevant measurements or parameters. One example is one or more electrode-based micro-sized sensors on or in the microneedle(s) either directly contact a plant xylem or phloem or other tissues for measurements, or indirectly draw constituent liquid from the xylem or phloem or other tissues for measurements, such as by diffusion, capillary action, or active pumping into a hollow microneedle. Each needle can include a single sensor or multiple sensors. If multiple sensors, they can measure the same parameter or different parameters.

3) Optionally, microfluidic techniques can be used to promote the access and transduction of measurements to promote reliable and accurate results. For example, selection of size and form factor of microfluidic channels or spaces in the needle forms can promote minimal invasiveness and good access to fluid content of plant tissue, soil, manure, or cells, and constituents, to be measured.

4) An interface allows capture of the transduced measurements. Circuitry or techniques provide power to any electrical-powered elements (e.g. electrode-based sensing elements and the ability to measure electrical properties at or about the electrodes). The captured measurements can be stored on-board to apparatus, partially processed on-board, or transferred to other components (via wire or wireless) for further use. In one example power and data transfer to and from the sensor(s) allow sensor operation and readout. The interface can be wired or wireless.

5) Reliable sensor insertion. This includes installation on a plant, insertion in water or soil or manure, or manipulation into a cell. The sensor assembly can include techniques to help retain the assembly in relevant position and make it robust and durable including for a wide range of operational and environmental conditions.

6) Various combinations of these and other features presents a sensor system that is relatively small form factor for minimal invasiveness of the fluid of a plant xylem or phloem or other tissues for any of variety of chemical, biological and physical parameters and is practical and economical with respect to placement and operation.

In one aspect of the invention, a sensor assembly includes a housing or printed circuit board, a probe extending therefrom, and on-board circuitry to take a relevant measurement related to the probe, and store, convert, or communicate it for further use. The form factor of the assembly is quite small, including miniature and even the micro-scale. In one example, a probe could be in microneedle having a tip with less than the width of a typical cell (e.g. less than or equal to approximately 5 micrometers; animal and plant cells generally have diameters of 5-20 micrometers). These form factors can vary but predominantly the combination is relatively very small such that it is minimally invasive or disruptive of the medium in which it is emplaced. Depending on the relevant medium, variations to these components will be made. In some cases, the probe will be needle-shaped (either hollow or solid), in others it can have a blunt distal end, can be rod-shaped or plate-shaped. In some cases, if wireless communication is used, the assembly can basically be sealed up and completely insertable or immersible in a medium. In other cases, it can either have a port or plug interface around an external device to plug into and communicate.

In another aspect of the invention, the ability to obtain relevant measurements with a miniature sensor or sensors, in combination with making those measurements accessible by a reader allows substantial flexibility in use of and measurements with such sensors. As indicated above, accessing in planta to plant tissues is one. Emplacement or insertion completely in medium such as soil or water is possible. In some circumstances, they may essentially be disposable.

In an aspect of the invention related to in planta sensing, an apparatus comprises a sensor assembly probe that can be implanted or inserted at a plant with minimum invasive but, because of small form factor of the implanted or inserted portion, take relevant measurements or interrogate the desired plant tissue. A miniature circuit is operably connected to active electrical or electronic sensing elements in the probe. The circuit also includes an interface which would receive wireless electrical power for the sensing elements as well as provide wireless data telemetry to send sensor measurements to a remote receiver. This avoids requiring a wired electrical connection to the sensor elements or an on-board battery and allows smaller form factor for implanting or inserting into the plant.

In one specific example of sensing nitrogen uptake in plants, the probe comprises a solid or hollow microneedle insertable to the location in the plant tissue where measurement is desired. Each sensor uses a micro-circuit with two or more electrodes to test electrical properties of the fluid of a plant xylem or phloem or other tissues either directly or indirectly contacted by the microneedle. One example of the electrodes is ion-selective active sensing elements, for example ion-selective field effect transistors (ISFETs), are placed in or on the microneedle. In the case of hollow microneedles, the form factor (outside diameter, needle distal point, orifice size, and interior hollow of the microneedle) is designed to promote reliable and automatic uptake of plant fluid into its hollow interior of fluid by capillary action or diffusion. The plant fluid contains nutrients (e.g., N, P, K, etc.) in concentrations that can be measured with the sensor electrodes. The sensor(s) (e.g. ISFET's) can be modified by positioning a membrane made of nanofibers on the gate of the FET. The membrane is configured to promote capture or trapping of nitrates. A measurement event is activated by receipt of power through the sensor interface by each ISFET. The membrane promotes precision and accuracy by presenting trapped nitrates at the ISFET and excluding other ionic species. By known methods, the ISFETs feedback electrical information to the sensor circuit that can be converted into data. The data can be read from the interface by a wire-connected reader or wirelessly by a remote reader. The reader can communicate the data to a processor which can derive nitrogen level.

In another aspect of the invention, a method of monitoring plants comprises minimally-invasively accessing desired plant tissue, sensing chemical species of interest, and communicating the sensing for further use. One example is trapping ionic species of interest, obtaining electrical power wirelessly or by on-board or off-board wired condition, using the electrical power for ion-selective sensing of trapped ionic species, and reading the sensed measurement. Additionally, other plant constituents can be sensed in analogous ways. Examples are other nutrients in addition to nitrogen, a variety of hormones, pH, and glucose.

In another aspect of the invention, the sensor(s) or method(s) as above-described are included in a system which interfaces with an on-board, wired, or wireless source of electrical power and reader/transmitter of sensor data. A local or remote processor processes the sensor data into a relevant estimate related to the plant. In the example of nitrogen as the relevant estimate, the sensor data can include nitrate concentration data that can be converted into estimated nitrogen level.

In another aspect of the invention, the system as above described can be operably connected or in communication with other systems. For example, the relevant estimates can be further processing, stored, compiled, or otherwise used.

In the example of nitrogen levels, these estimates can be stored and then analyzed over time for research purposes related to such things as understanding plant nitrogen uptake or use. It can also be combined with other information. For example, the nitrogen level estimates can be correlated to such things as time, soil characteristics, weather, or the like to evaluate interaction between environments and plant genotypes.

Another aspect of the invention comprises using a plurality of sensors with one or just a few wireless sources. The wireless sources are configured to provide electrical power and read sensor data from any of a plurality of the sensors. In one example, plural sensors are implanted or inserted at a variety of plants over an area of a field. A wireless source is located in the field. The wireless source can both supply wireless operational power and read sensor data to any and all of the widely distributed sensors.

In another aspect of the invention, the miniature sensor assemblies can be configured in a variety of ways. One example is to have just one sensor per assembly. Another is to have plural sensors on each assembly. The plural assemblies can be all configured to sense the same thing (e.g., nitrogen) to promote accuracy of measurement, or configured to measure different things (e.g., nitrogen, phosphorous, potassium, etc.) at the same location in the plant. Furthermore, one sensor assembly per plant can be installed or plural sensors per plant to measure at different plant locations of the same plant. One or more sensors can be placed on plural plants across an area or field or population, or multiple such areas, fields, or populations. Data from such widely distributed sensing can be communicated and beneficially compiled over time.

In another aspect of the invention, techniques can be used to install each sensor to a plant. Examples include clips, adhesive, clamps, or combinations. Furthermore, techniques to make the sensors robust and ruggedized in any environment can include sealing at least portions of the assembly.

Another aspect of the invention is designing the microscale form factors and at least some of the additional functions of the sensor assembly with microfabrication techniques in an efficient and effective way. One example is using silicon and microelectromechanical systems (MEMS) based microfabrication of not only the micro needle but also at least some of its fluidic properties and the sensor elements.

Further objects, features, aspects, and advantages of the invention will be more apparent from the following description.

III. BRIEF DESCRIPTION OF THE DRAWINGS

The appended drawings illustrate certain features of the invention, as will be further discussed below:

Figure 11A:
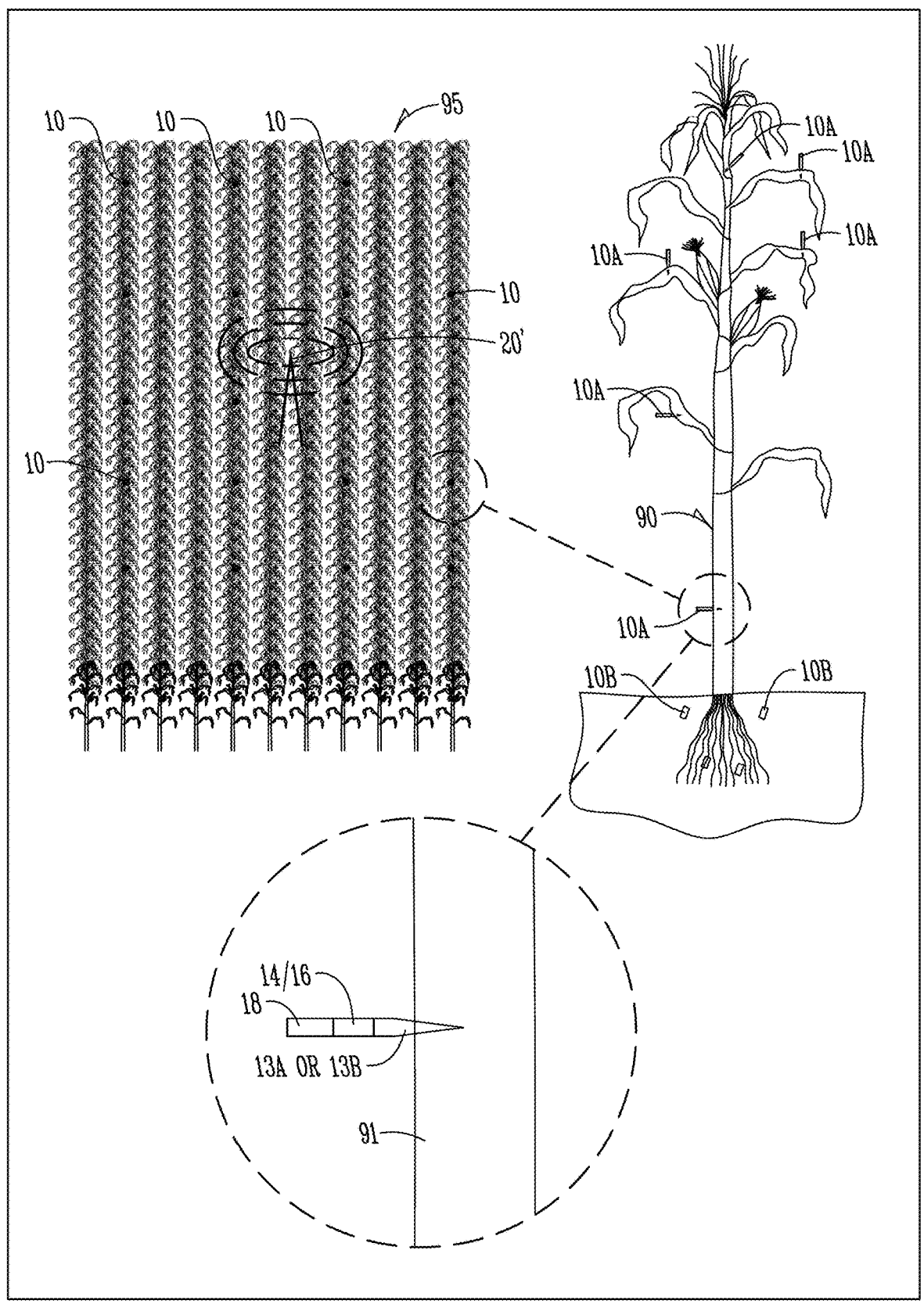

FIG. 11A is a set of diagrammatic illustrations of aspects of the invention applied to in planta sensing, including a widely-distributed set of microsensor assemblies installed on a plurality of different plants in a field with a centralized power and data transmission source (left side image), an enlarged view of one of the plants showing how plural sensor assemblies can be installed per plant (middle image), and a greatly enlarged and not to scale diagram of a one microneedle sensor installed along a plant stalk (right side image).

Figure 11B:
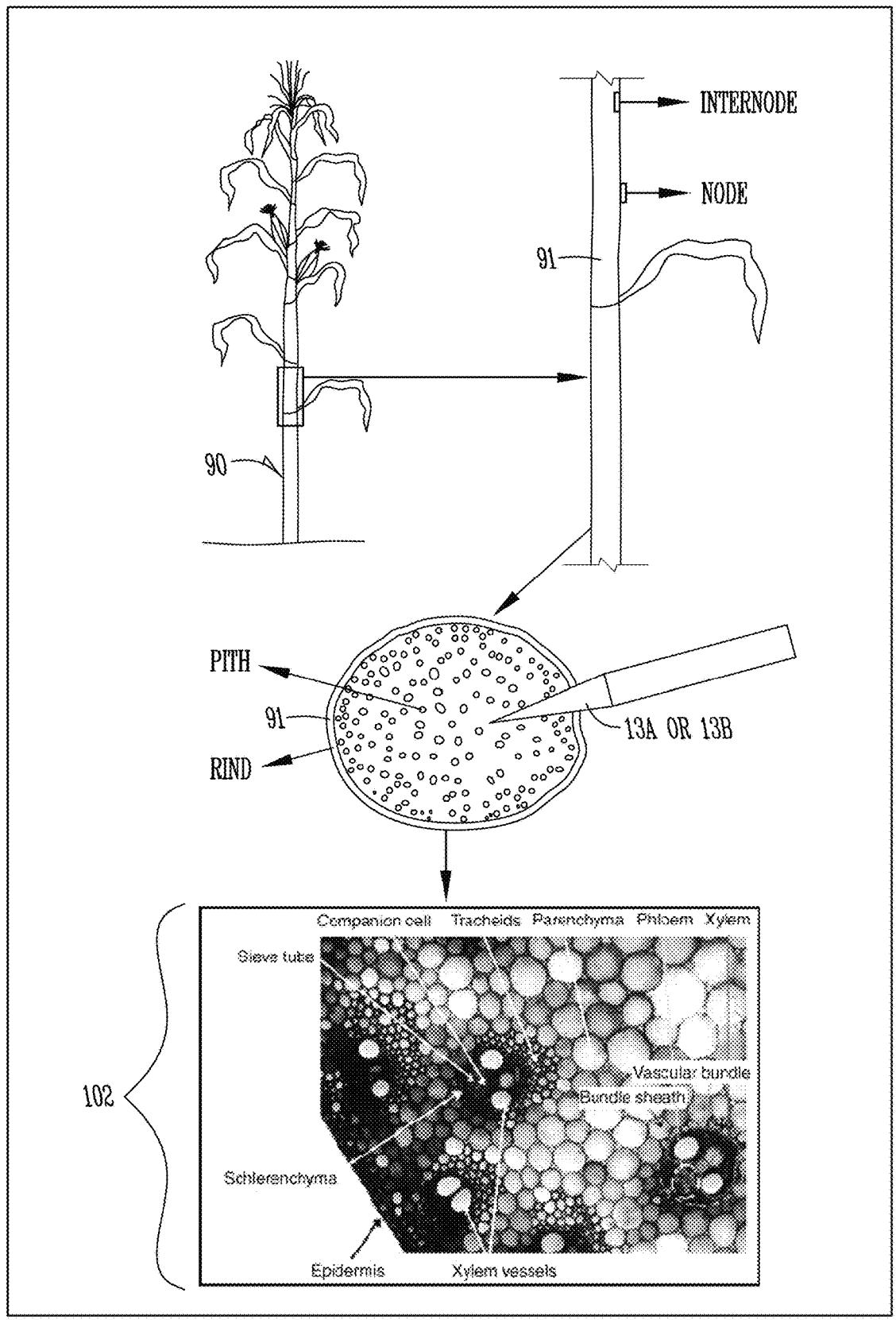

FIG. 11B is a set of diagrams showing the microneedle sensor of FIG. 11A penetrating the stalk into the plant xylem tissue to the xylem vessels and the fluid carried by them as a technique to access relevant plant tissue and chemicals.

Figure 12A:
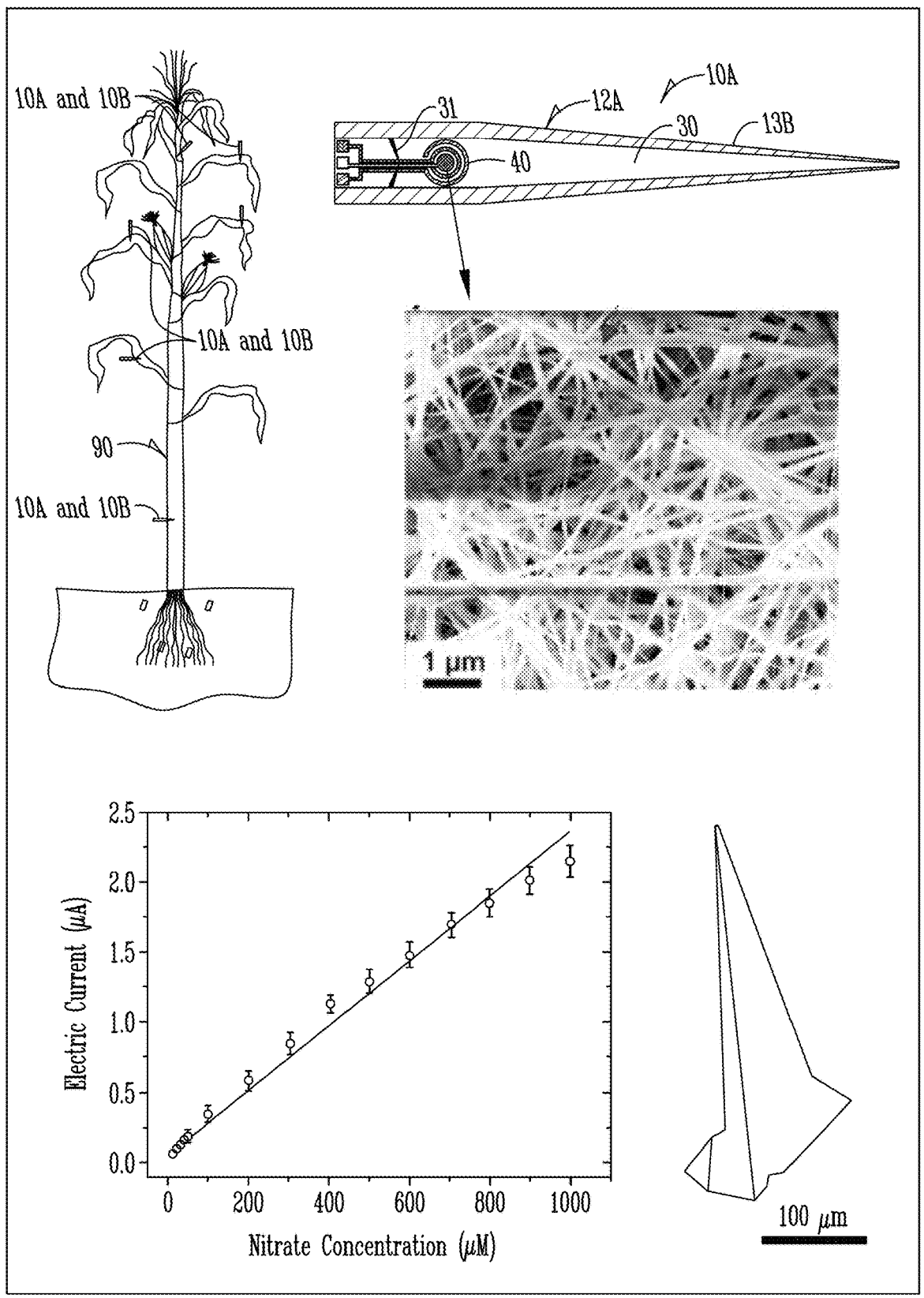

FIG. 12A is a group of illustrations related to a first specific exemplary embodiment of a sensor probe according to the invention, including (a) a diagram indicated probe placement on a maize plant, (b) a greatly enlarged cross-section diagram of probe tip and internal microfluidics and specially-modified ion-selective electrical sensor element, (c) still further enlarged image of nano-fibrous mat on the sensor element; (d) graph establishing experimental results at sensing nitrate concentration with such a sensor, and (e) greatly enlarged image of the probe microneedle distal end.

Figure 12B:
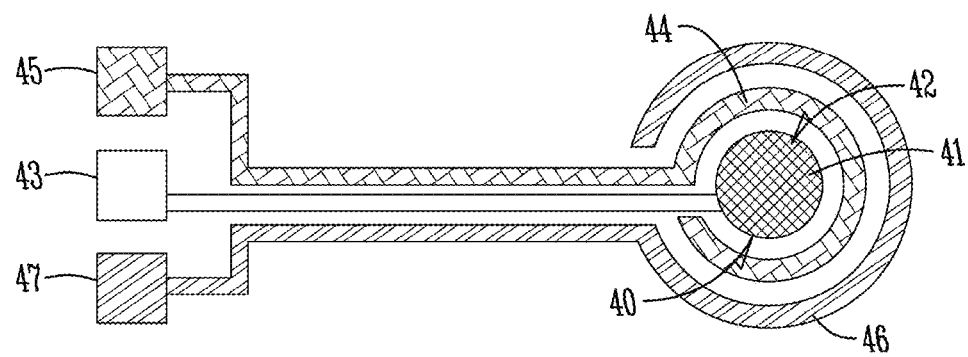

FIG. 12B is an enlarged view of the nitrate sensing element of FIG. 12A.

FIGS. 13A-E are a group of illustrations related to a second specific exemplary embodiment of the invention including (FIG. 13A) maize plant placement, (FIG. 13B) probe in perspective, (FIG. 13C) an enlargement of distal end of probe and a ISFET as the ion-selective active sensing element of the probe, (FIG. 13D) magnified images of plural ISFETs made by MEMS manufacturing techniques, and (FIG. 13E) graph of experimental results for nitrate concentration measurements for different probe configurations.

Figure 14:
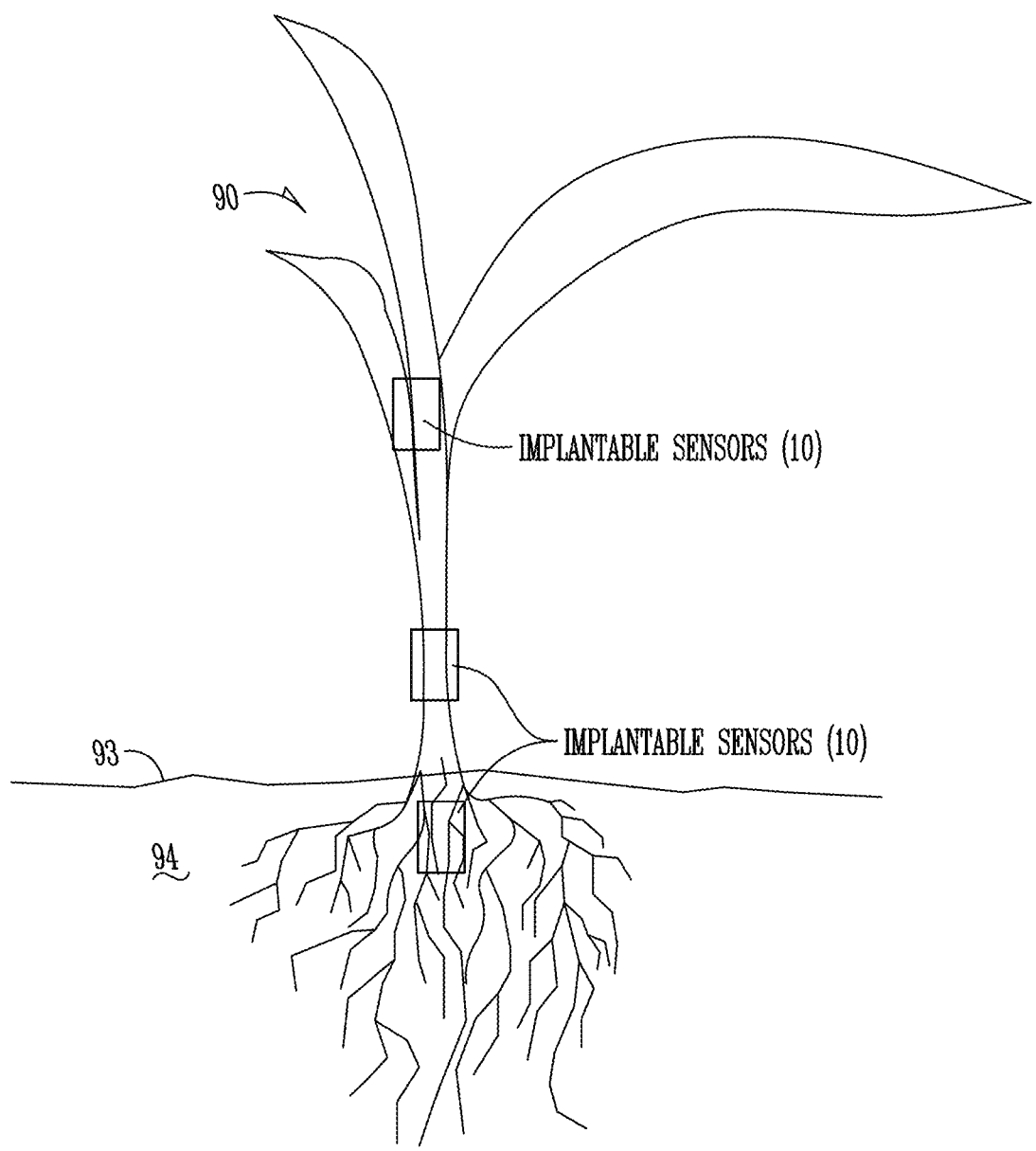

FIG. 14 is a highly diagrammatical illustration of a maize plant and possible probe installation locations.

Figure 15A:
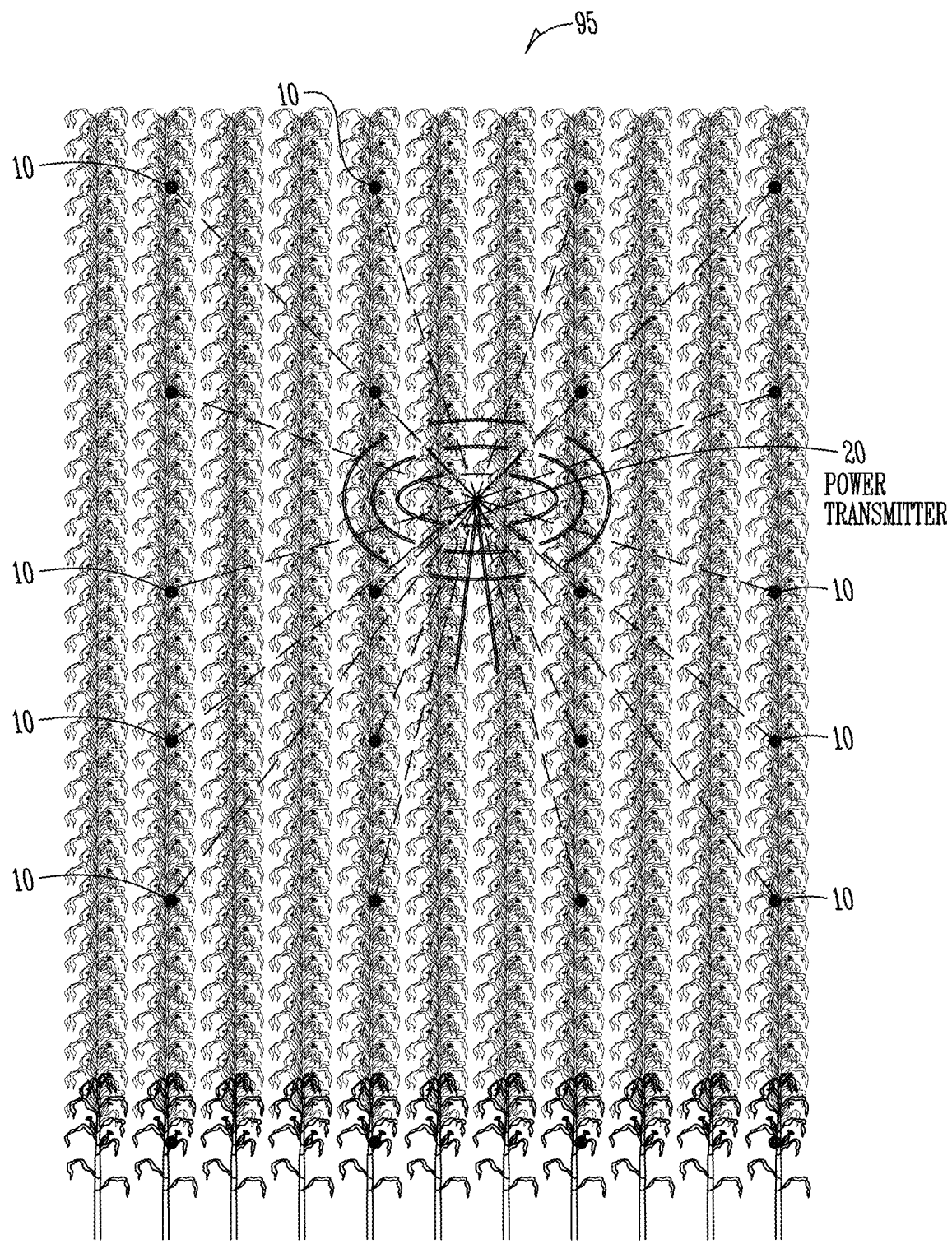
Figure 15B:
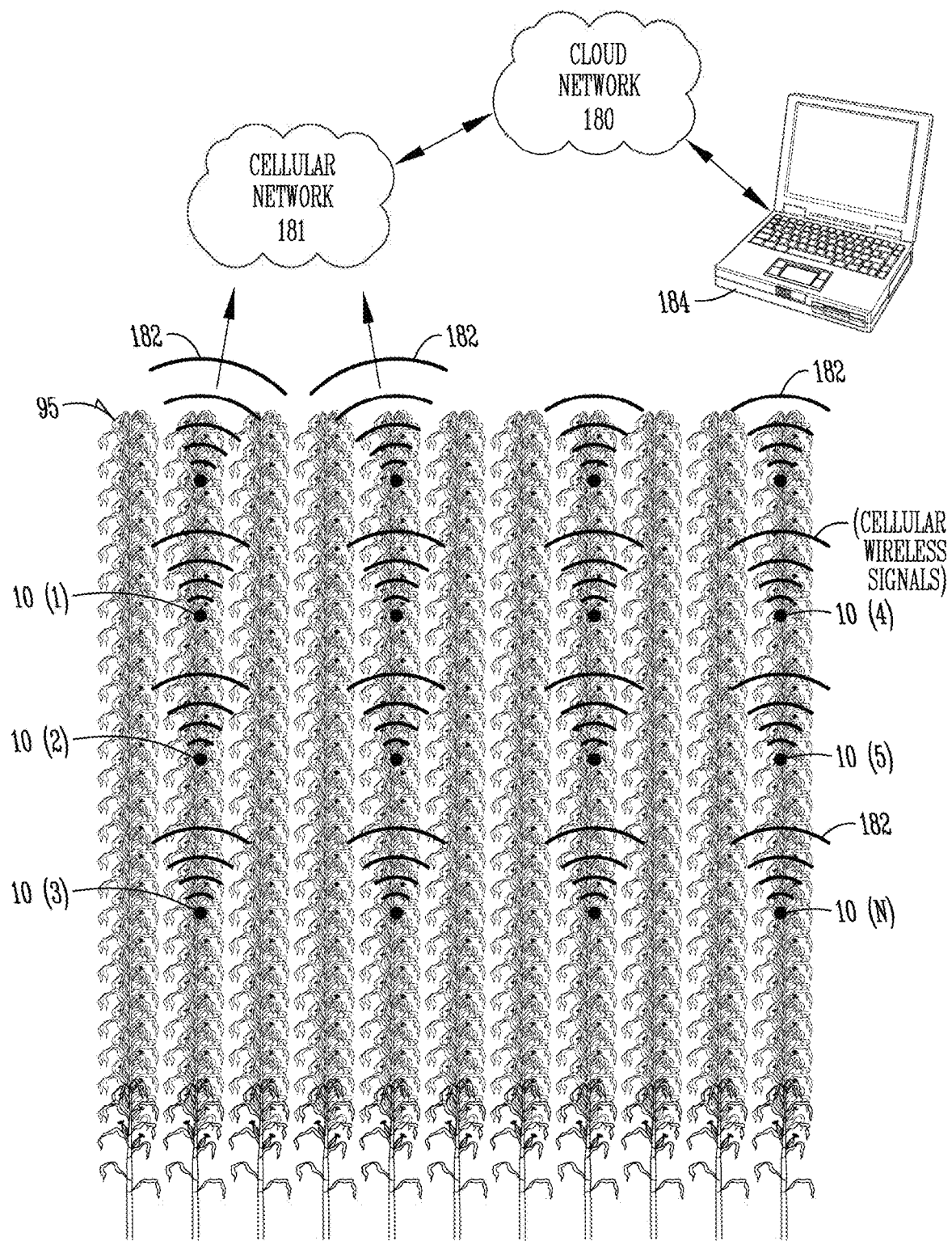
Figure 15C:
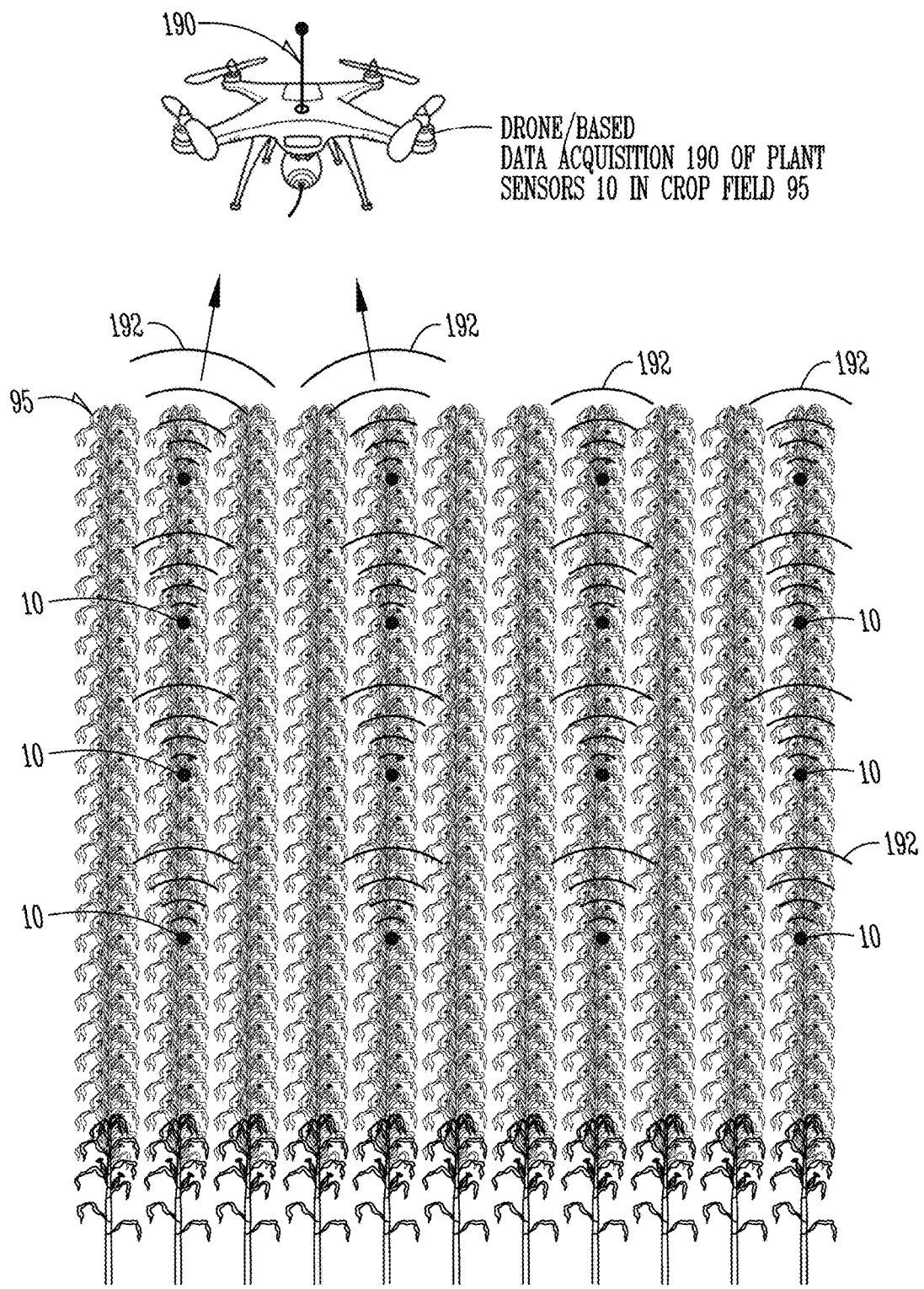

FIGS. 15A-C are diagrams illustrating systems according to another aspect of the invention showing a plurality of the probes installed in maize plants around a field with a central wireless power and data telemetry station for the probes (FIG. 15A), cellular to cloud network data acquisition (FIG. 15B), or drone-based wireless acquisition (FIG. 15C).

Figure 16A:
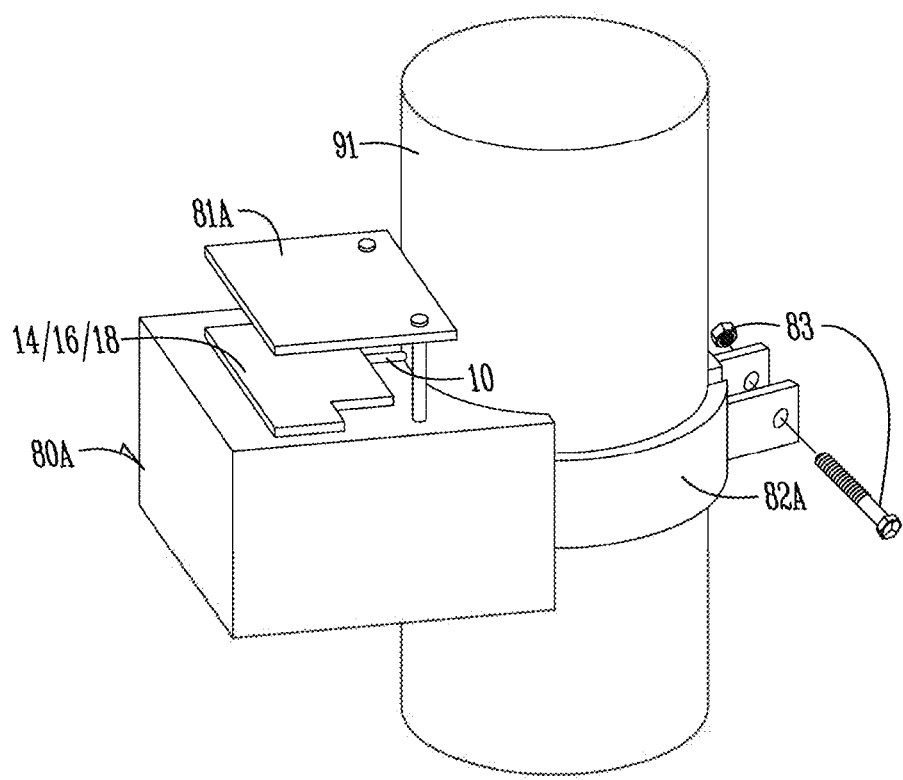
Figure 16B:
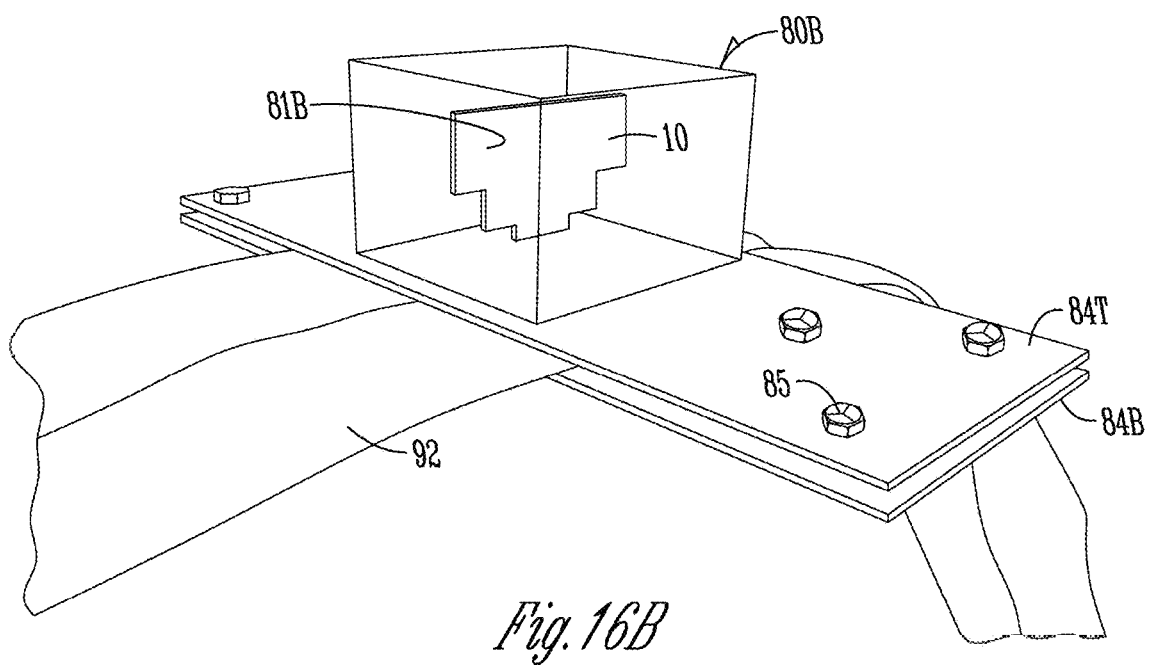
Figure 16C:
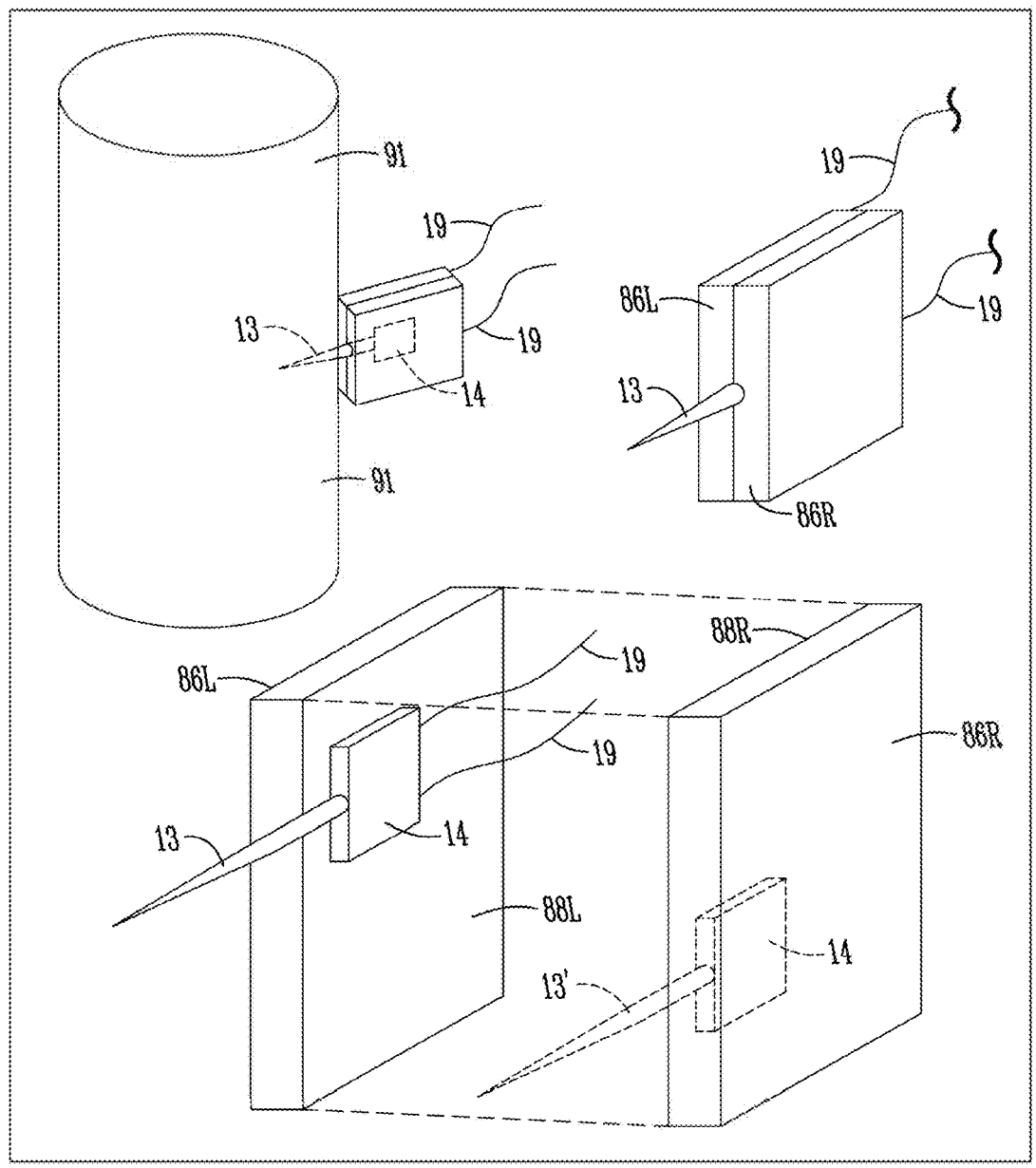
Figure 16D:
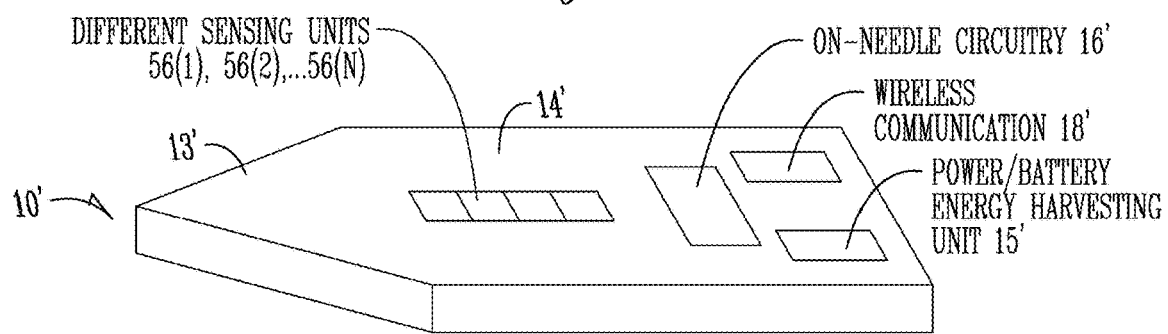
Figure 17A:
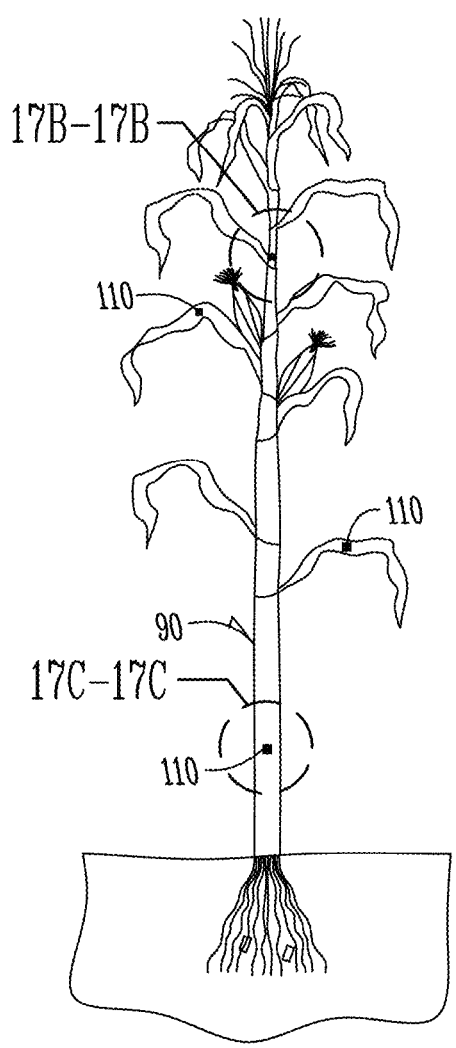
Figure 17B:
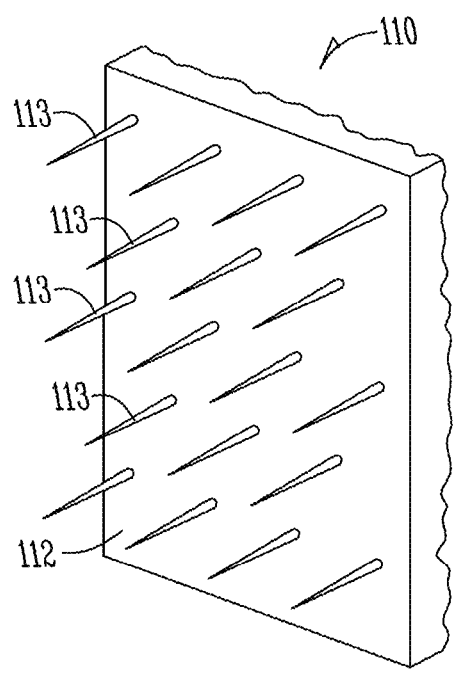
Figure 17C:
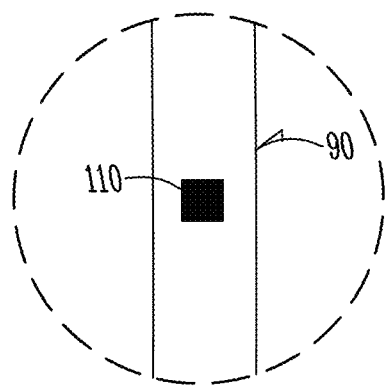
Figure 17D:
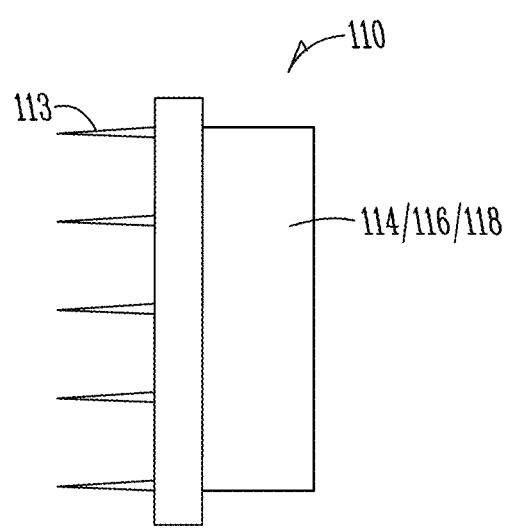

FIGS. 16A-D are a group of diagrams illustrating alternative mounting and installment techniques for microneedle probe assemblies. For example, special "holders" for keeping the probe fixed to the plant are shown as non-limiting examples, namely, a clamp around a plant stalk in FIG. 16A and a clamp across a plant leaf in FIG. 16B. A sandwich of a microneedle held between thin foam pads is shown in FIG. 16C. FIG. 16D is a highly diagrammatic view of a fully integrated device according to one embodiment of the invention.

FIGS. 17A-D are diagrams of an alternative embodiment according to the present invention, in particular, to a multi-needle sensor assembly fabricated by MEMS techniques. Examples of the types of measurements possible with it include but not limited to ion species such as nitrate, phosphorous, sulfate, and potassium, and hormones such as jasmonic acid, salicylic acid, and indole-3-acetic acid.

Figure 18A:
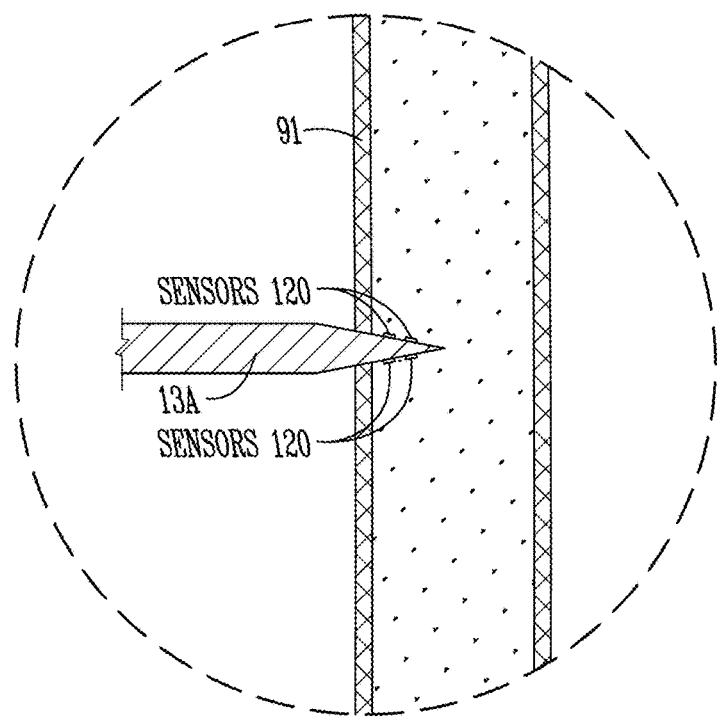
Figure 18B:
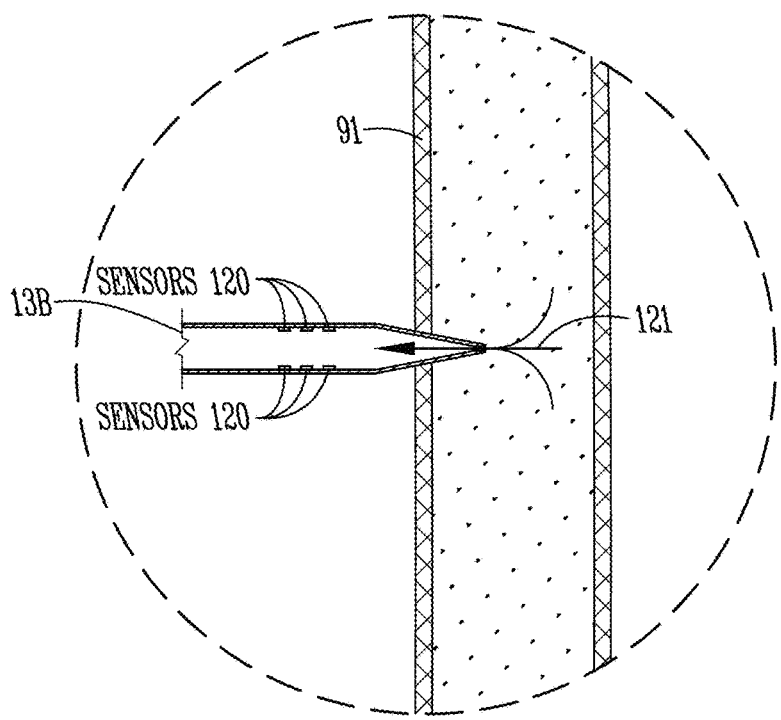

FIGS. 18A and B are diagrammatic examples of either solid body microneedles or hollow microneedles, and how they can support from one or many sensor elements. FIG. 18A illustrates direct contact sensors to plant xylem with solid microneedle. FIG. 18B illustrates indirect contact sensors to plant fluid drawn into a hollow needle by capillary action.

Figure 19A:
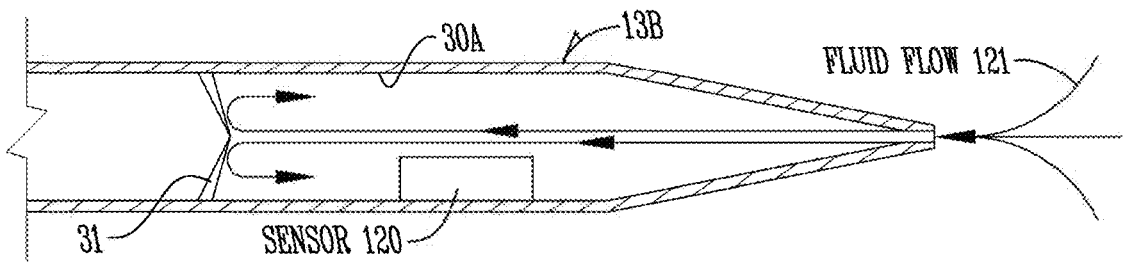
Figure 19B:
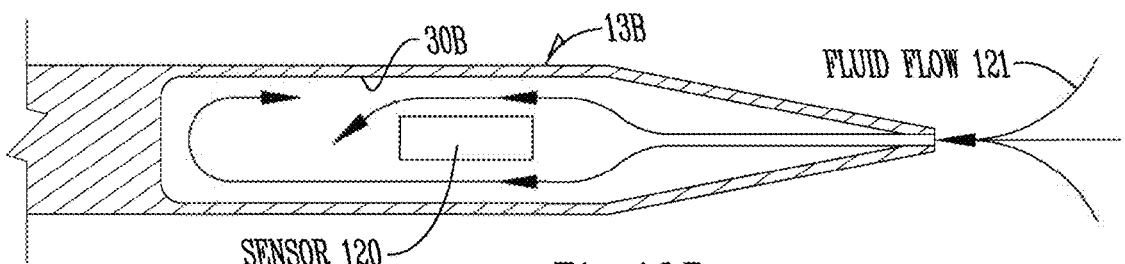
Figure 19C:
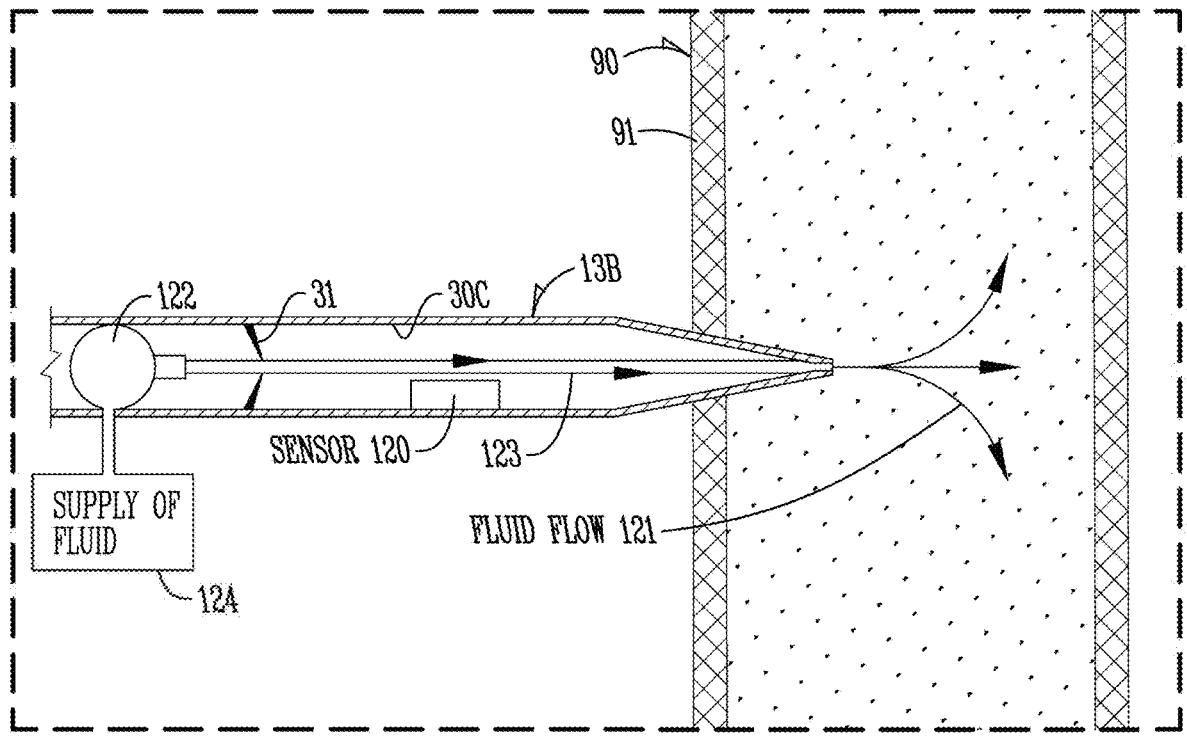

FIGS. 19A-C are diagrammatic examples of different microfluidic configurations for hollow microneedles including a one-way valve to contain a fluid sample for sensing (FIG. 19A), an enclosed interior space for the fluid sample (FIG. 19B), and the alternative of using microfluidic circuits and components to optionally infuse or pump fluid from an external supply into the plant (FIG. 19C).

Figure 20A:
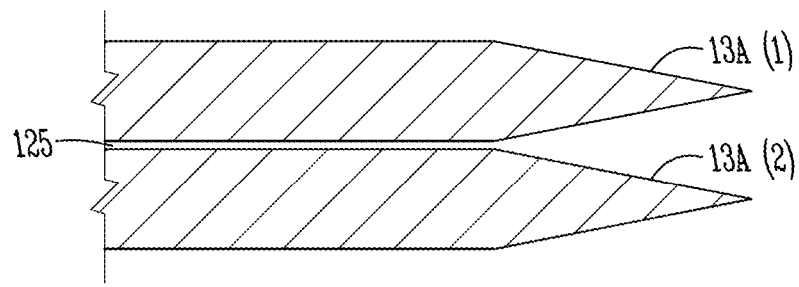
Figure 20B:
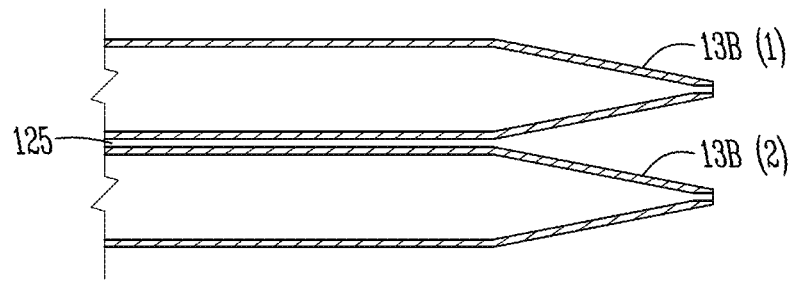

FIGS. 20A and B are still further alternative embodiments for the microneedle assembly. FIG. 20A is a double-needle (solid cross section) for greater mechanical strength. FIG. 20B is similar but with side-by-side hollow needles.

Figure 21A:
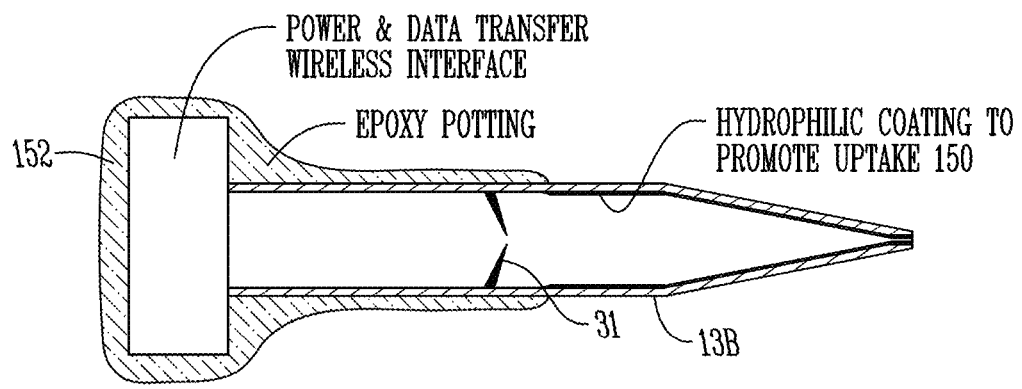
Figure 21B:
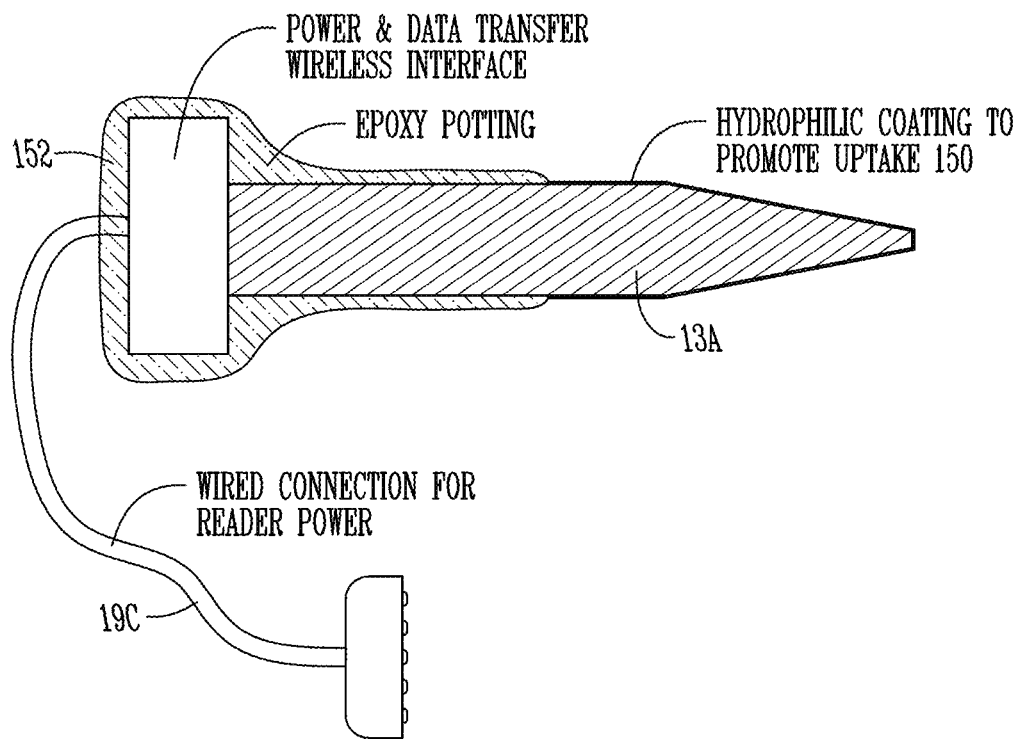

FIGS. 21A and B are highly diagrammatic illustrations of additional potential features that can be used with the exemplary embodiments. Hydrophilic coatings of the distal microneedle end can promote capillary uptake. Potting materials (e.g. epoxy) could be used after fabrication, assembly, and set up on the plant to protect at least some of the assembly from moisture, dust, or potentially damaging forces.

Figure 22A:
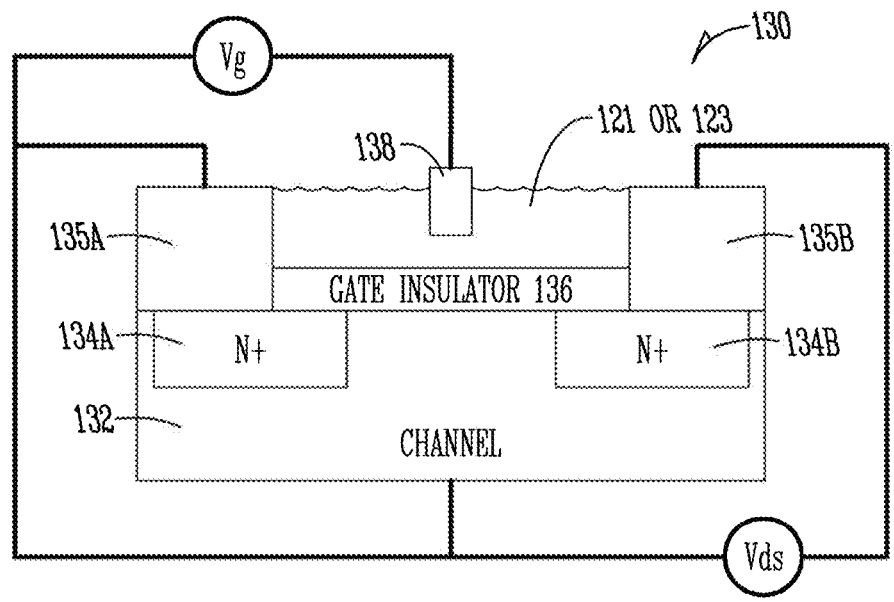

FIGS. 22A and B are simplified and not to scale diagrams showing three electrode sensor circuits (left side) and two electrode sensor circuits (right side) of the general type that could be used with the exemplary embodiments.

Figure 23A:
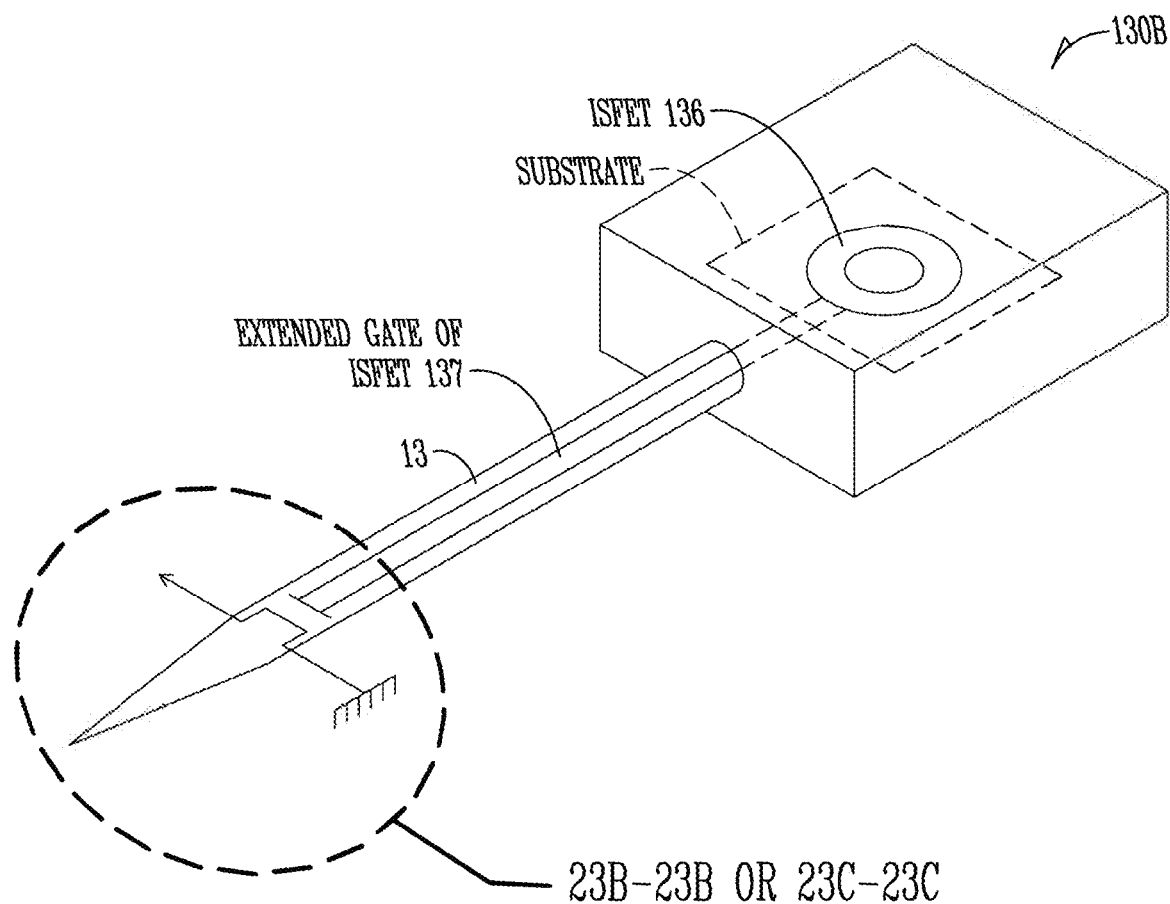
Figure 23B:
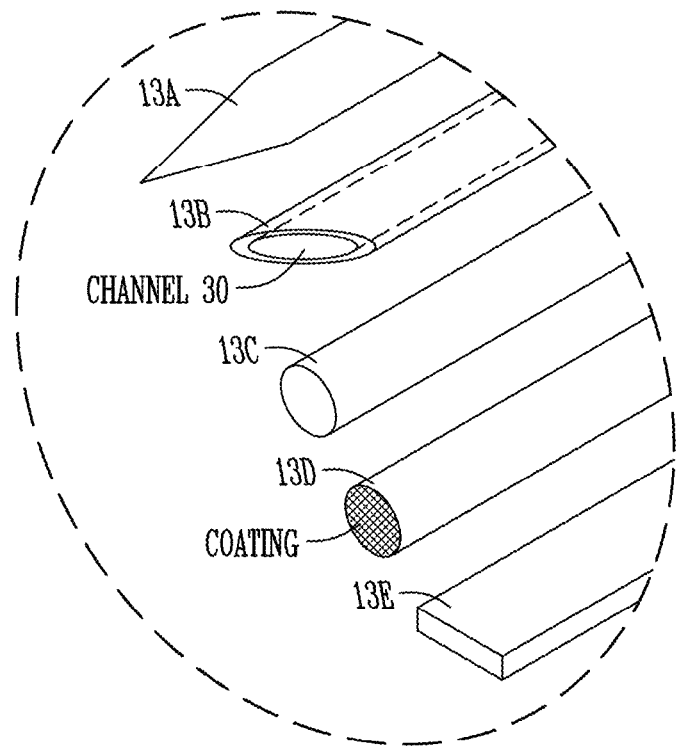
Figure 23C:
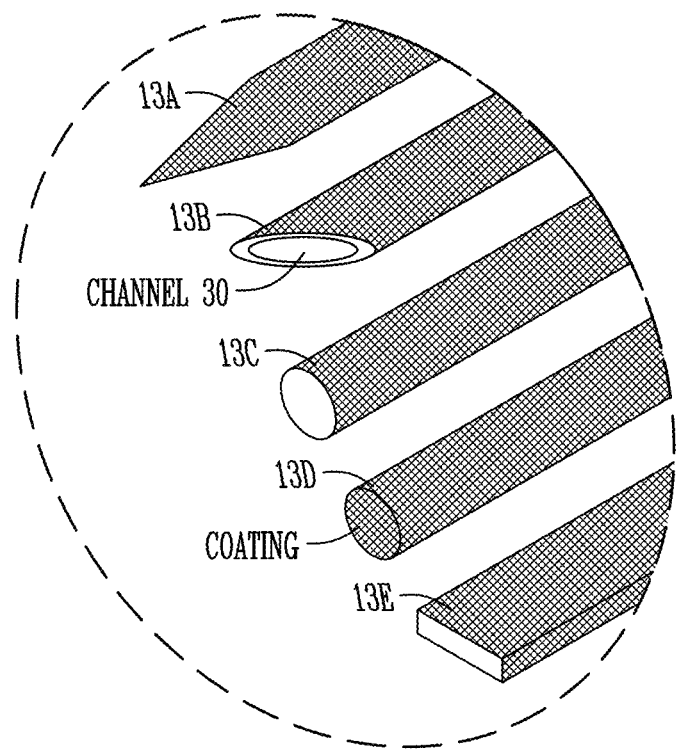

FIGS. 23A, B, and C depict an optional alternative probe, particularly use of an extended gate ISFET circuit as a part of the measurement circuit. FIGS. 23B and C show different non-limiting examples of probe tip configurations; FIG. 23B with different tip form factors; FIG. 23C with different tip form factors and coatings.

Figure 24:
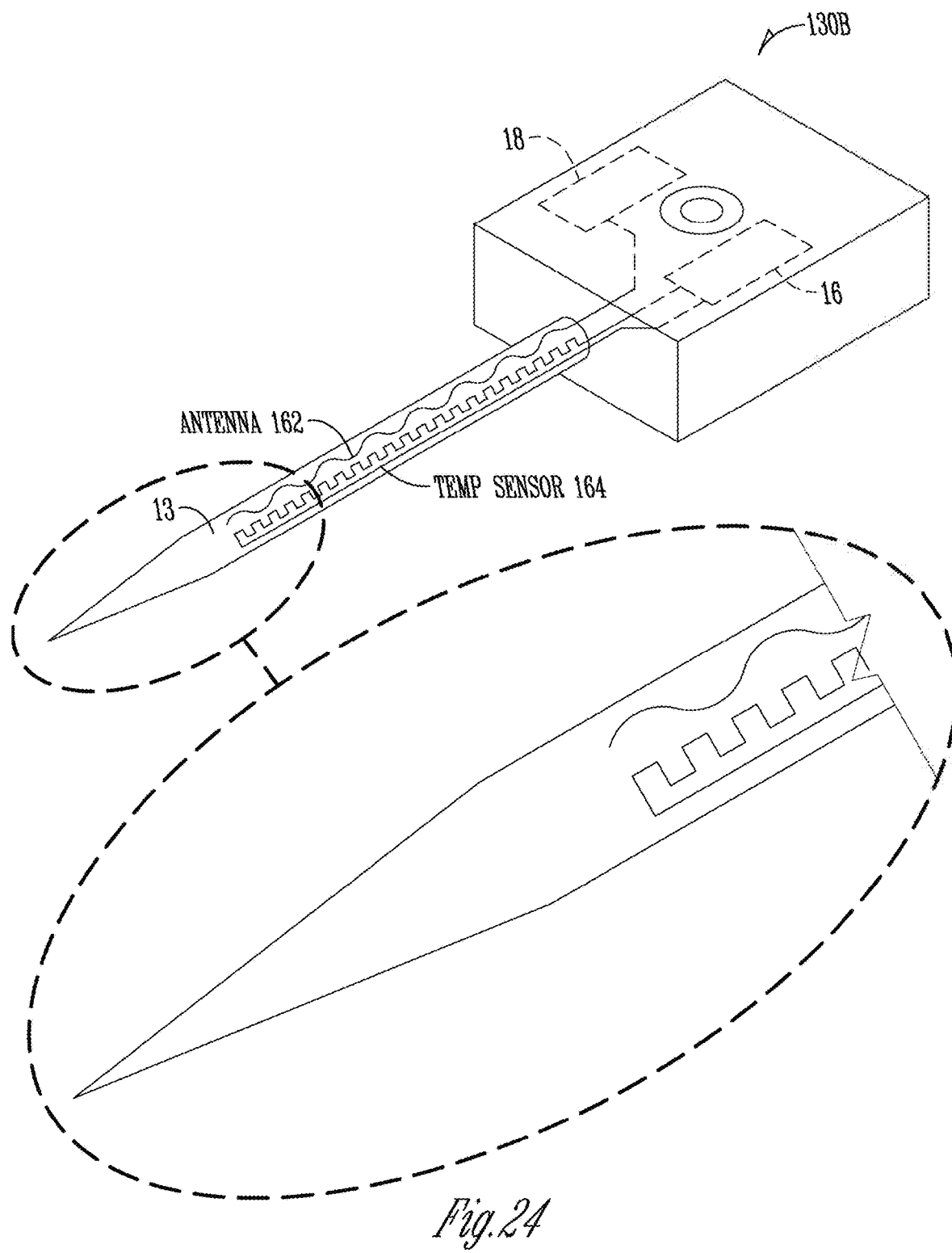

FIG. 24 is similar to FIG. 23A but illustrates the optional addition of other active elements to the sensor assembly, in this case an antenna for wireless communication and a temperature sensor that can concurrently or on its own take temperature measurements of the medium in addition to the measurements taken via the probe.

Figure 25A:
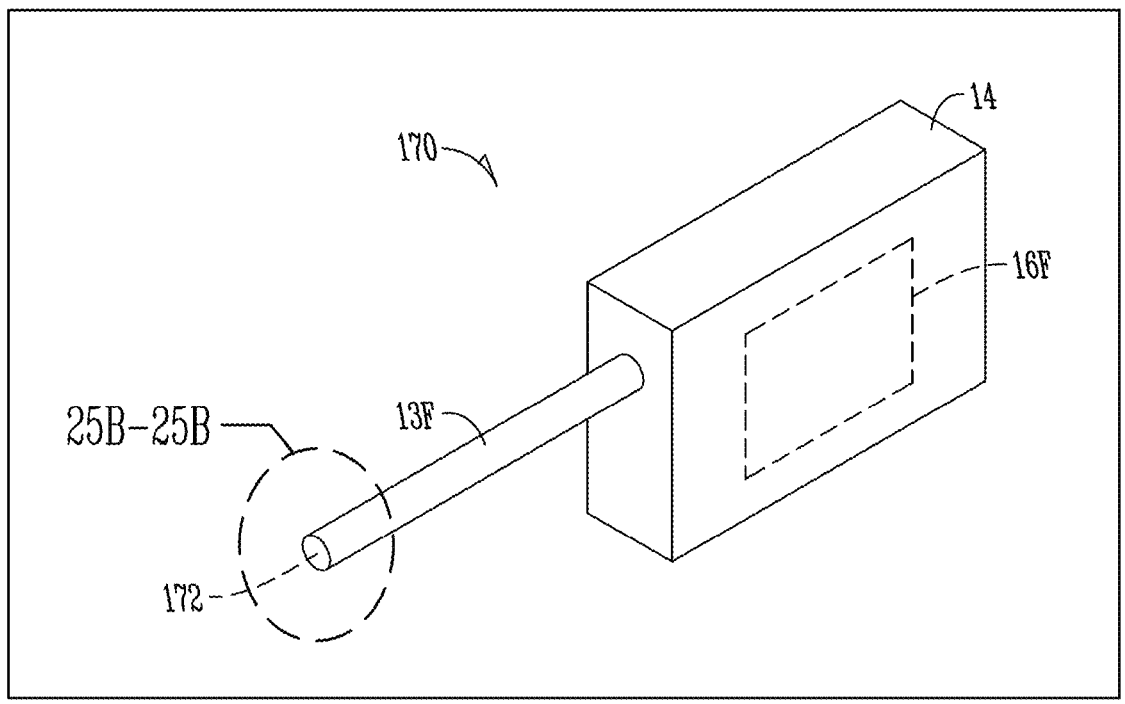
Figure 25B:
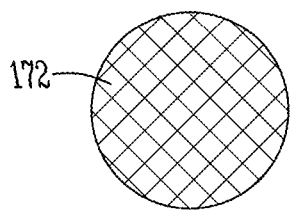
Figure 25C:
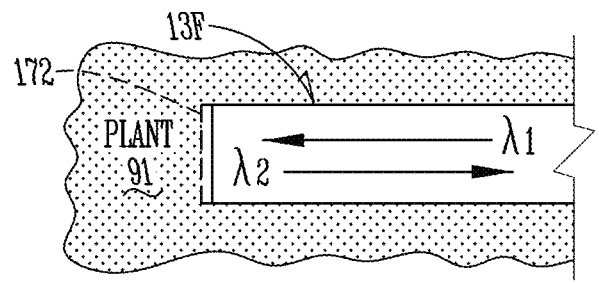

FIGS. 25A-C illustrate an alternative embodiment of a sensor assembly according to the invention with a different measurement technique than electrode-based; here an optical-based sensing technique for obtaining optical measurements of the medium. FIG. 25A shows diagrammatically the probe tip being comprised, at least in part, of an optical waveguide (e.g. optical fiber); FIG. 25B is an enlarged end view of the optical waveguide of FIG. 25A illustrating diagrammatically that the distal tip surface could include a coating or other functionalized surface that can enhance or be used with optical sensing; and FIG. 25C shows in enlarged scale diagrammatically how light energy could be emitted from an optical circuit in the sensor assembly body, through the wave guide to its distal end, and into the medium (e.g. plant, soil, water, etc.) under investigation; and how, according to well-known optical sensing/detection techniques, a return of light energy from the optical boundary between the wave guide and the medium under investigation can be guided by the waveguide back to an optical detection circuit, where differences between the emitted and return light (e.g. resonant wavelength or light intensity offset) can be, by calibrations or otherwise, used to derive measurement of some characteristic of the medium under investigation.

Figure 26:
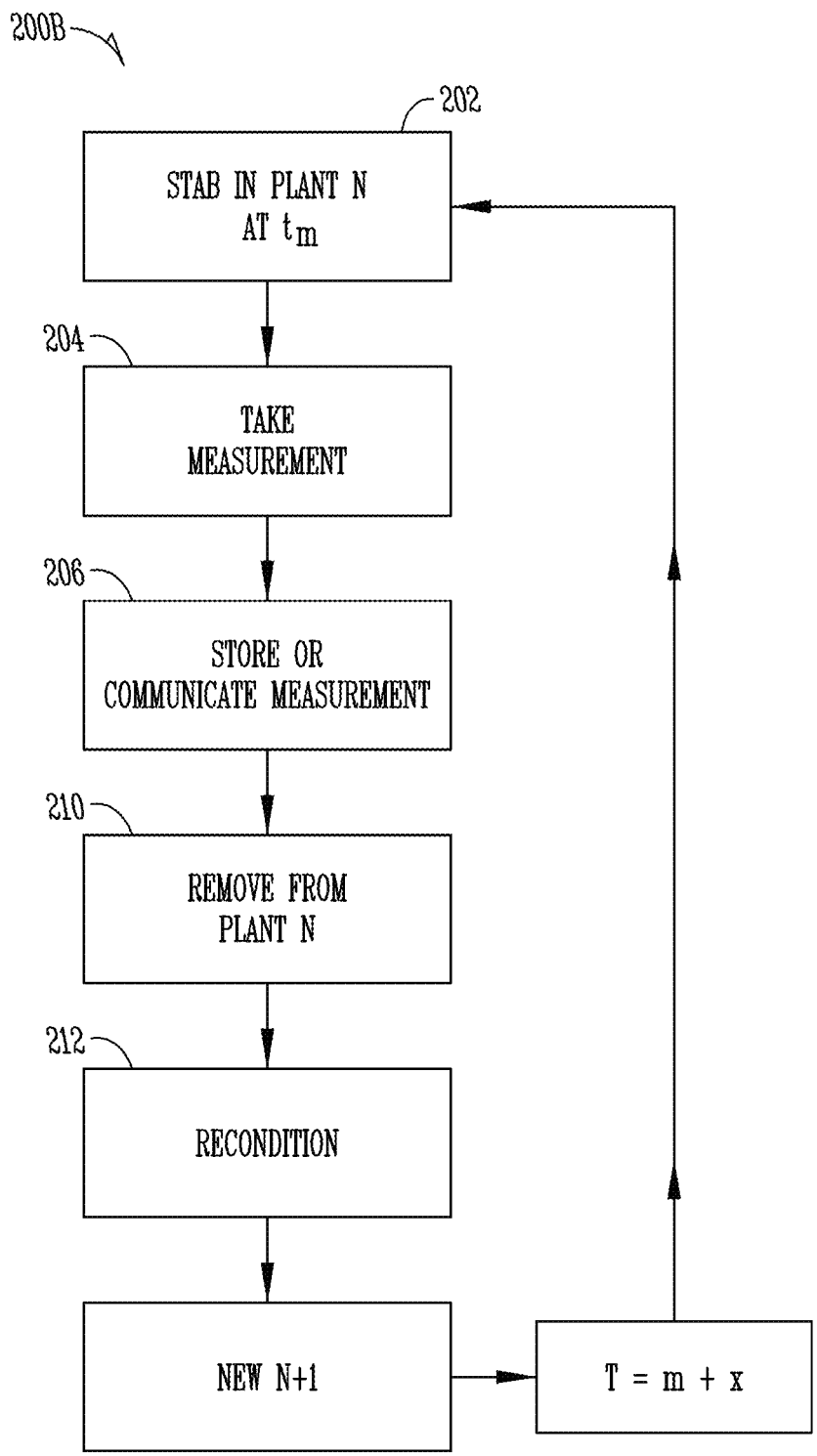

FIG. 26 is a flow chart of an alternative possible method of use of an in planta microneedle-based sensor as described above.

IV. DETAILED DESCRIPTION OF EXEMPLARY EMBODIMENTS OF THE INVENTION

A. Overview

For a better understanding of the invention and its various aspects, several examples of how it can be implemented will now be described in detail. It is to be understood that these examples are neither inclusive nor exclusive of all forms and embodiments the invention can take.

For example, some examples will focus on in planta derivation of nitrogen levels in maize by using ion-selective sensors to measure nitrate concentration of the plant at or near the sensor location in the plant. It is to be understood that other ionic species can be measured in analogous ways. Likewise, other chemical compounds, constituents, or parameters can be measured in analogous ways. It is to be further understood that, as described above and discussed further below, miniature probe-based sensors according to the invention can also be applied to a variety of mediums over and above plant tissue. Non-limiting examples include soil, fluid including water 112 FIG. 5, manure 114 FIG. 6, and individual cells 96 FIG. 7.

Furthermore, aspects of the invention involve ways for minimally invasive and cost-effective monitoring. Other types of sensors are possible for either a micro-needled probe or other probe shapes or configurations, and techniques of obtaining wireless power and data telemetry for the purpose of monitoring other than ionic species in the plant. Non-limiting examples of other sensed constituents include glucose, nutrients, hormones, toxins, biomolecules, DNA or other proteins, GMOs, to name a few. Those skilled in the art will appreciate how aspects of the invention can be applied beyond that non-inclusive list.

Variations obvious to those skilled in this technical field will be included within the invention.

B. Generalized Embodiment

With reference to FIGS. 1-10, in generalized form aspects of the invention pertain to quite small, relatively low-cost sensor assemblies for measuring any of a variety of measurables of a variety of mediums with a probe at down to micro-scale in size. Such a small probe and/or the whole assembly can penetrate, be inserted, or otherwise be placed in or into a relevant medium. A measurement circuit and interface to the probe can operate together for taking measurements. The circuit can store, process, convert, or communicate measurement data. As such, this very small sensor assembly is adaptable to be emplaced non-intrusively, and many times nondestructively into a medium under investigation, and yet have the ability to transduce for further use important information about the medium.

Figure 1:
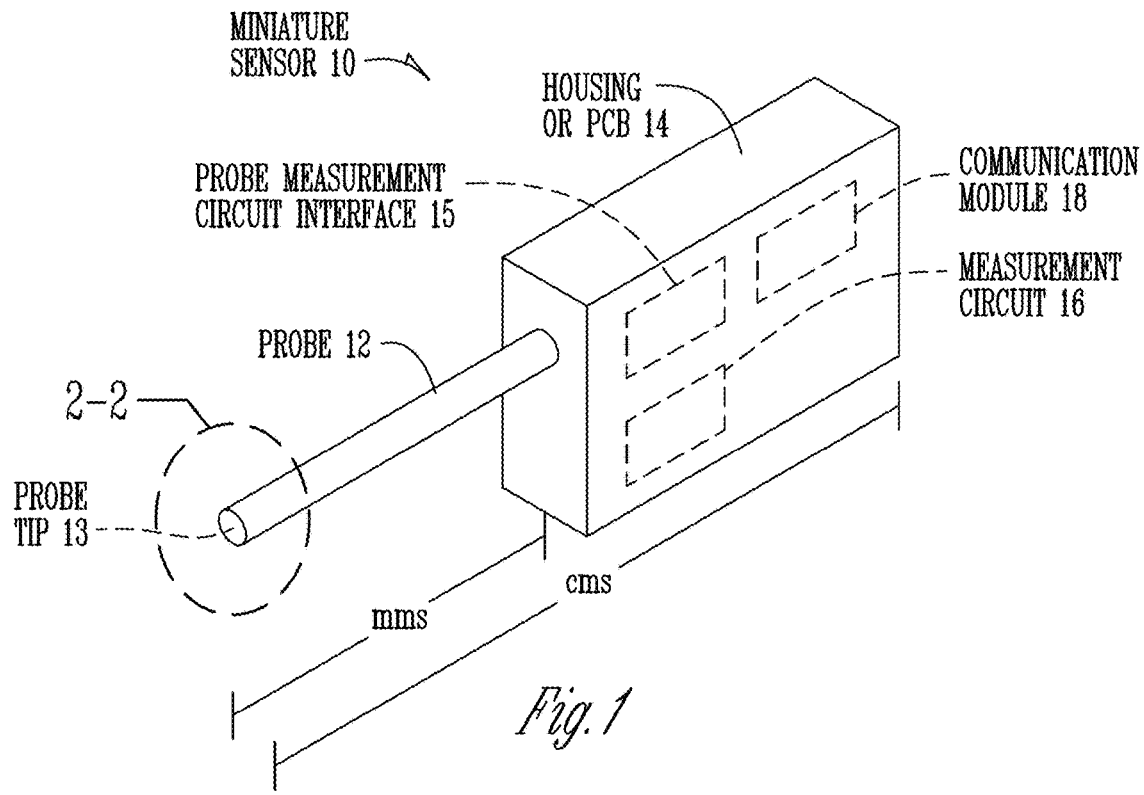
FIG. 1 is a greatly enlarged perspective view of a diagrammatic depiction of one example of a form the invention can take, including a housing (e.g., PCB) with a probe element extending therefrom. Internal components are shown in dashed lines.

FIG. 1 shows an example of such a micro-sensor assembly 10, which includes the elongated or outward extending probe 12 and a housing or PCB 14. Scale annotations are included to give the reader an idea that, through selection of appropriate components and assembly/fabrication techniques, the size can be quite small. In one example, the distal probe end 13 could be of a width much smaller than the width of a typical cell to allow insertion into that cell for sensing. A housing or PCB 14 can include in interface circuitry 15 between probe 12 and measurement circuit 16. It could also include onboard a communication module 18.

With such a form factor, as further described herein, one or many of these small microprobe assemblies 10 could be placed such as on the individual plants or parts of plants, relative to individual cells, buried in soil or dropped into water, or dropped into other viscous substances such as manure. Those skilled in the art are familiar with a number of sensing techniques that can measure a variety of parameters including biochemical sensing with relatively low power usage. This allows either micronization of the sensor assembly 10 and communication with a further device to provide such power and exchange data or signals.

Figure 2:
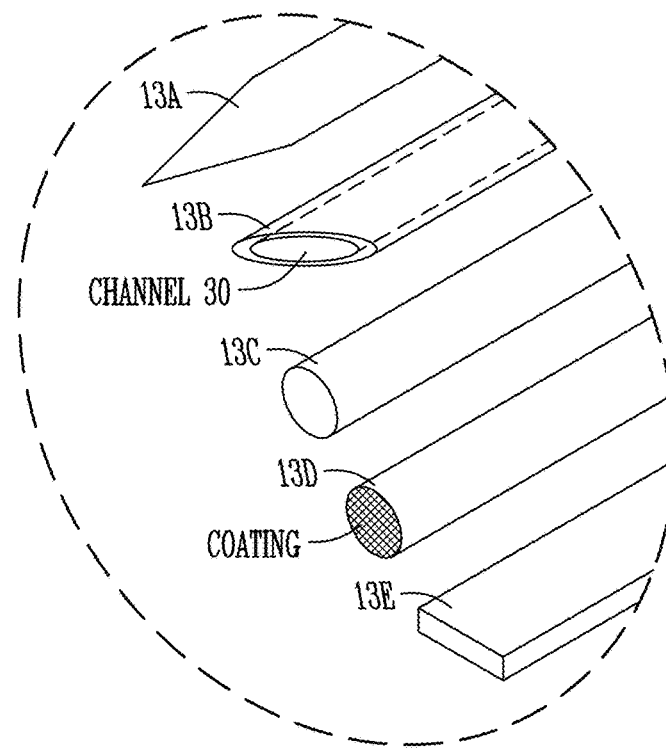
FIG. 2 is taken along line 2-2 of FIG. 1 and is a collection of non-limiting examples of distal probe tip shapes possible with the sensor assembly of FIG. 1.

FIG. 2 illustrates that probe tip 13 could have any of a number of form factors. Non-limiting examples are solid microneedle tip 13A, hollow microneedle tip 13B with accessible lumen or channel 30, solid or hollow rod-shaped blunt end 13C, and blunt end 13D including some type of functional coating or surface (one example being an optical interface or a nanomaterial coating), or other cross-sectional shapes such as square rectangular such as tip end 13E. And, of course, probe 12 could have the same shape along its length or different cross-sectional shapes. Furthermore, as further explained below, a sensor assembly 10 could have more than one probe 12 and/or more than one measurement circuit 16.

Figure 3:
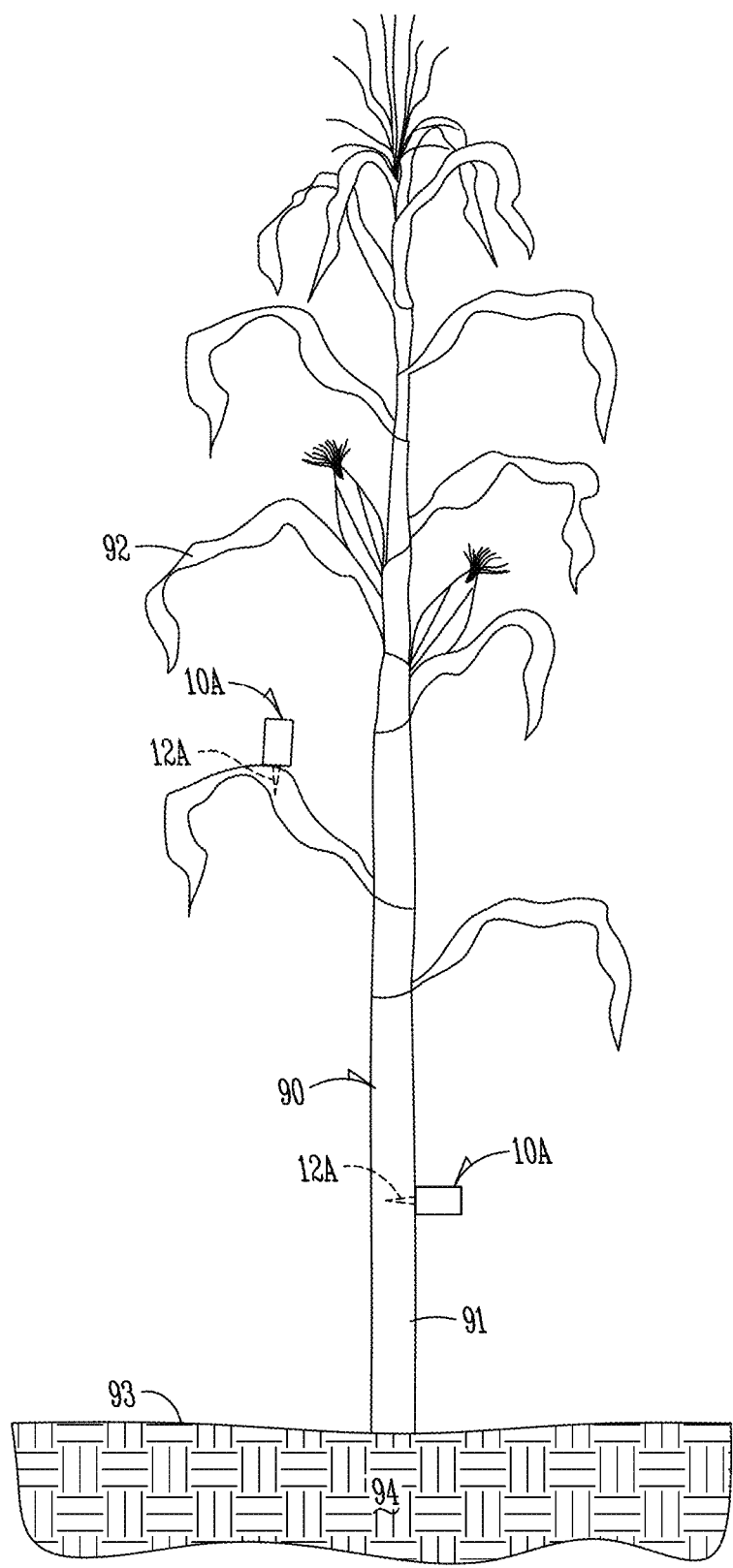
FIG. 3 is a reduced in scale diagrammatic depiction of a plant having two sensor assemblies of FIG. 1 in place in planta, one with a probe penetrating the plant stalk, the other with the sensor probe penetrating a plant leaf.

To illustrate the flexibility of use of assembly 10, reference can be taken to FIGS. 3-7. In FIG. 3, two sensors 10A with microneedle tips for probes 12A are essentially pushed into stalk 91 or leaf 92 of a growing plant 90. Thus, the small form factor and use of a microneedle to access internal plant tissue is nonintrusive and substantially nondestructive. It also allows, if desired, the sensors to essentially grow with the plant without material disruption of that growth. As illustrated in FIG. 3, the small size allows multiple sensors 10 per plant if desired. Such in planta sensing can provide the same measurement either at the same locations or at different locations on the same the plant, or different measurements from the same plant, including after the plant has emerged from the top of the ground 93 but is growing in soil 94.

Figure 4:
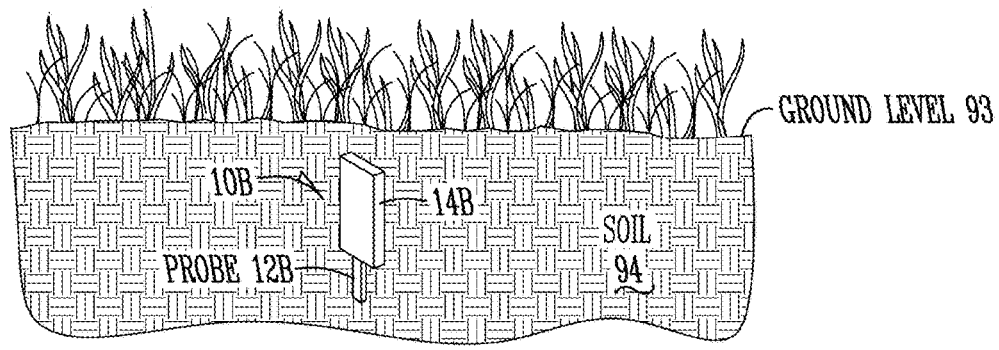
FIG. 4 is a highly diagrammatic view of a sensor similar to FIG. 1 inserted completely into soil.

FIG. 4 shows a sensor assembly 10B similar to that of FIG. 1 configured for soil measurements. Its probe 12B can extend from its housing 14B, which could be sealed off and fluid tight so that it can be essentially put underneath the surface 93 and into and completely encapsulated into soil 94 for taking soil measurements. Optionally, the probe 12B (or a portion of it) can be coated with a hydrophilic material to attract fluid (e.g. soil, water) to sense.

Figure 5:
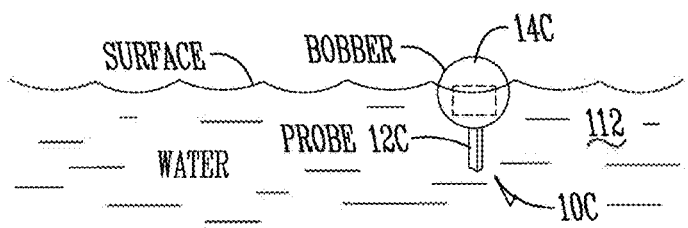
FIG. 5 is a diagrammatic depiction of a probe assembly like FIG. 1 with the probe inserted into a quantity of water and the body floating.

In contrast, FIG. 5 illustrates a similar form factor of sensor assembly 10. A probe 12C extends from housing 14C. The sensor 10C can simply be dropped into water (e.g. a pond a, lake, a stream, an animal water feeder, etc.). Housing 14C can contain the essential circuitry needed to take and acquire a measurement. It can be sealed and fluid tight. It can be configured to either sink, float, or stay somewhere in between. A discussion of deriving nitrate measurements from water, including with functionalized graphene materials on the probe, can be found at Ali, et al., Electrochemical detection of nitrate ions in soil water using graphene foam modified by T102 nanofibers and enzyme molecules, DOI: 10.1109/TRANSDUCERS.2017.7994032, Conference: The 19th International Conference on Solid-State Sensors, Actuators and Microsystems (Transducers 2017), Kaohsiung, Taiwan, incorporated by reference herein.

Figure 6:
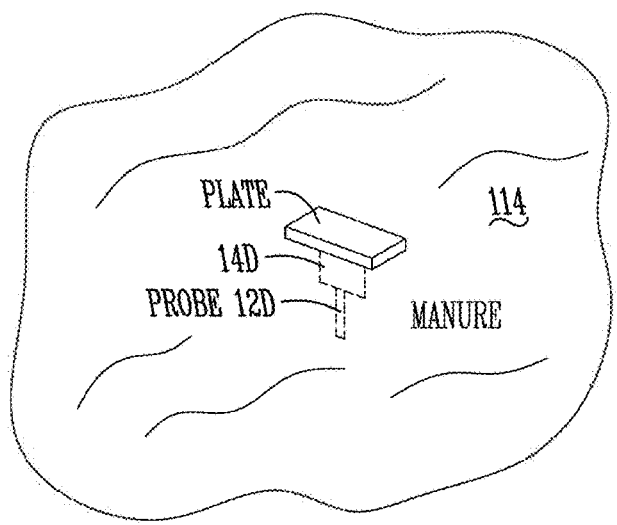
FIG. 6 is a highly diagrammatic view of a probe similar to FIG. 1 having at least its probe portion inserted into a quantity of manure.

FIG. 6 illustrates sensor assembly 14D with probe 12D and diagrammatically depicts it as inserted into a viscous medium such as animal manure. Its probe can contact and take biochemical measurements relevant to that medium.

Figure 7:
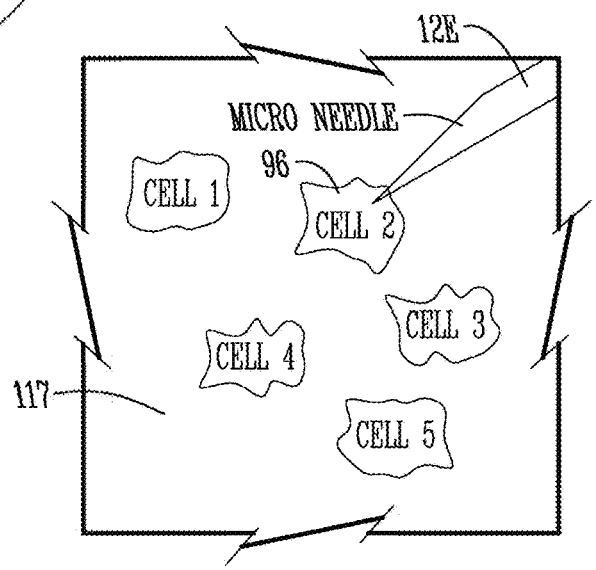
FIG. 7 is a highly diagrammatic and highly enlarged scale depiction of a probe end in the form of a micro-needle such as could be used with a sensor assembly of FIG. 1, but with the distal microneedle end inserted into a cell.

FIG. 7 shows diagrammatically and greatly enlarged, a field of view 117 of a microscope with a microneedle 12E having a tip inserted into a cell 96. As can be appreciated by those skilled in the art, a variety of well-known microscopy and cell investigation techniques and systems are available to assist the user to locate a cell of interest and then manipulate a microneedle into the selected cell. An example of that was simply a microneedle adapted for accessing a cell to either infuse it or remove material from it as described in US patent publication US 2004/0029213A1 to Callahan et al. entitled "Visual-Servoing Optical Microscopy" which is incorporated by reference herein and includes a description of penetrating a cell with a probe and extraction and infusion.

Figure 8:
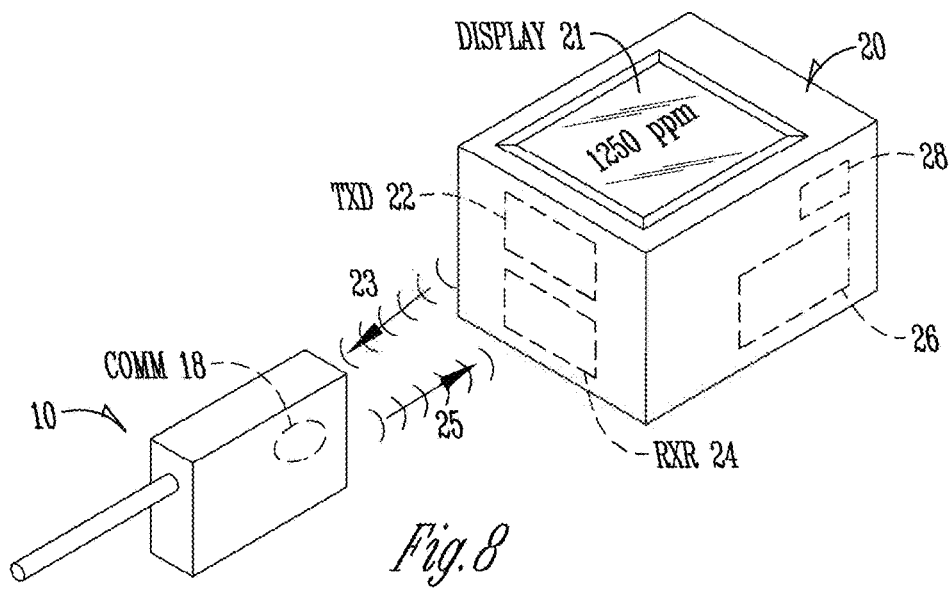
FIG. 8 is a diagrammatic depiction of a probe such as FIG. 1 adapted for two-way wireless communication with a device which can read the measurements from the probe, process them, and/or communicate them to a still further device.
Figure 9:
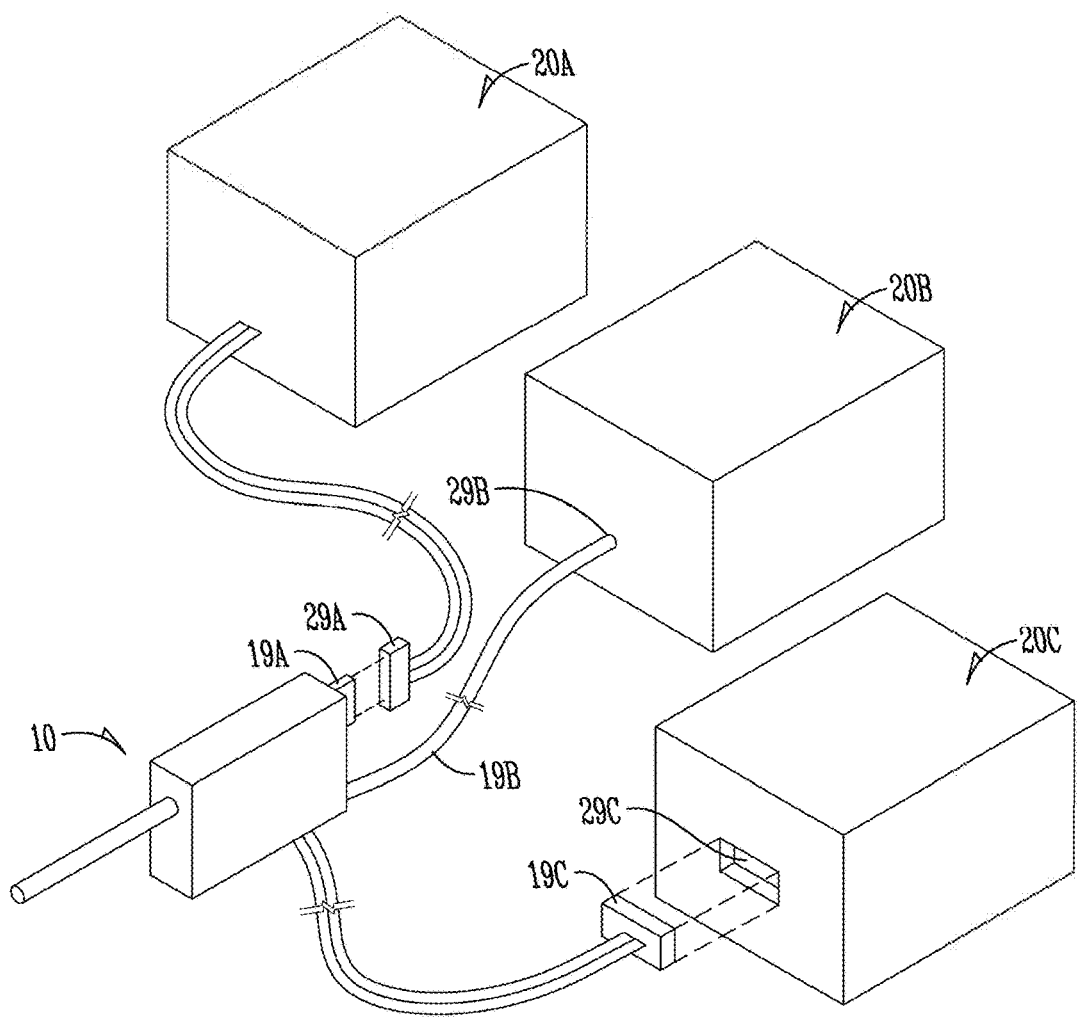
FIG. 9 shows a probe similar FIG. 1 but illustrates several alternative ways the probe assembly can be read and communicated with; namely some sort of plug-in on the probe body, a hard-wired cord away from the probe body to a plug for device 20, or directly hardwired between the probe body and the other device.

FIGS. 8 and 9 are intended to show how a microsensor assembly such as FIG. 1 can communicate information and data for further use. One example in FIG. 8 is simply an on-board communication module 28. It can be accessed wirelessly by a reading device 20 to communicate measurement data 25 to device 20. In some cases, a communication module 18 (e.g. Bluetooth®) can also receive data from device 20 or another device. It can also, in some cases, receive electrical power via such radio energy 23. An example of the same can be found at US patent publication US 2011/012431 to Theilmann et al., incorporated by reference herein. This would allow power to be wirelessly transmitted and/or induced on the sensor so that an onboard battery is not required. As further indicated at FIG. 8, reader 20 can be of a variety of types with a variety of functionalities. U.S. Pat. No. 7,797,367 to Gelvin, incorporated by reference herein describes such wireless reading of data from a sensor circuit and/or communication with a sensor circuit. For purposes of general discussion, reader 20 could include a transmitter 22, receiver 24, some sort of processor 26 and its own communication module 28 for wired or wireless communication with still further devices, networks, or systems. See, e.g., U.S. Pat. No. 6,889,165 to Lind et al., incorporated by reference herein. It could also include of course on-board storage as can measurement circuit 16 of the sensor assembly itself. As illustrated in FIG. 8, the reader could have a display 21 (e.g. LCD or other) that could have a graphic user interface (GUI); here showing, as but one example, display of a nitrate concentration reading from sensor 10 of "1250 ppm". A user would be able to immediately visually see the measurement.

Alternatively, as illustrated in FIG. 9, sensor assembly 10 can have other modes of communication with another device such as any of reader unit examples 20A, B, or C. One example is simply exposed electrical leads 19A at the body of sensor 10. A reader 20A with appropriate plug 29A could plug into those exposed leads 19A for one way or two-way communication.

An alternative reader 20B could simply be hardwired connected to sensor 10 at 19B and 29B. A further alternative reader 20C could have a port 29C mateable with a plug 19C that it is hardwired to sensor 10 for similar functionality.

As can be appreciated, the wireless configuration of FIG. 8 has advantages, particularly if the sensor assembly 10 is inserted in a medium and not accessible directly while in the medium. The possible range of wireless communications can vary. Presently, ranges of a few inches to a few feet, and even further are possible. The designer can choose what is appropriate based on balancing factors such as need, cost, size, complexity and the like.

Figure 10:
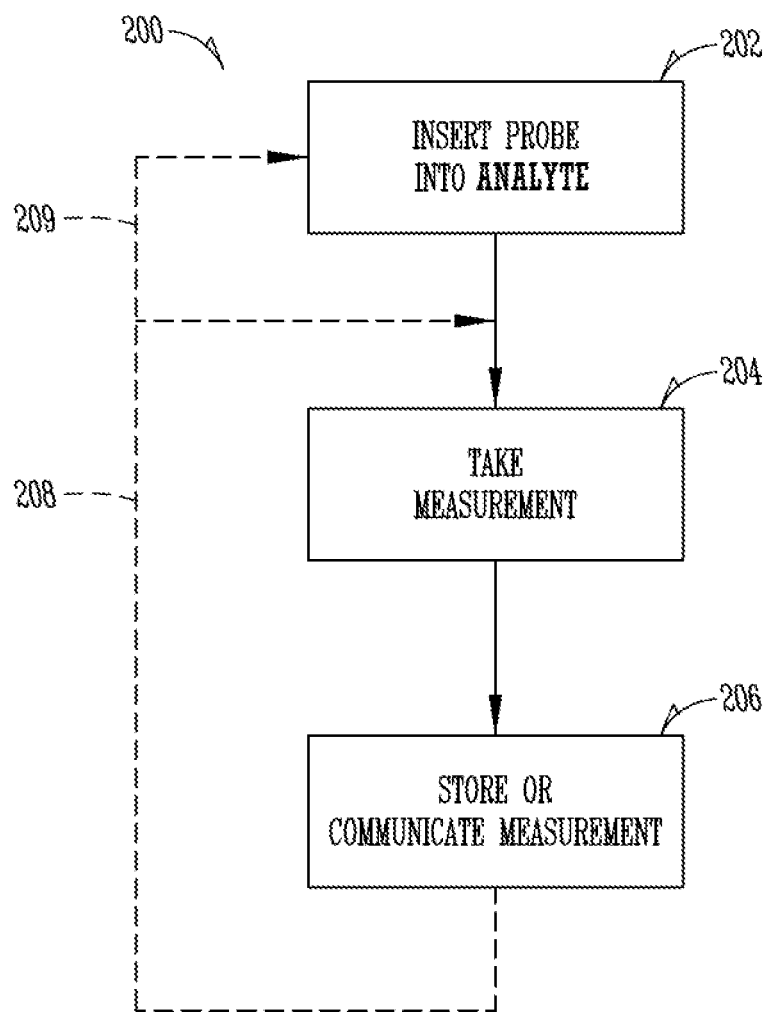
FIG. 10 is a flow chart of one non-limiting methodology of use of the probe such as FIGS. 1-9 according to one example of a method of the invention.

FIG. 10 is a very simplified flowchart of one non-limiting example of a method 200 for use of sensor 10 or its different adaptations. The small probe assembly (e.g. assembly 10) can be inserted into the target medium or analyte (step 202). A measurement with the probe and measurement circuit of the sensor 10 is taken (step 204) while inserted in the medium. The on-board circuitry of the probe stores the measurement or comments on cases, converts it into data. As indicated above, that also can be communicated in any of a number of ways (step 206).

Importantly, probe/sensor 10 can be used in a variety of different ways. One example is a one-time measurement. But also because of its small size and unobtrusiveness, once emplaced in a medium, it could be used to numerous measurements. They can be over relatively shorter (e.g. fractions of seconds) or relatively larger separations in time (e.g. seconds, minutes, hours, days, weeks, months). As indicated above, if left in place on a growing plant, measurements spaced-apart temporally can provide important information about how that measurement varies over time, growing conditions, and otherwise. If placed in soil, similar temporally-relevant monitoring is possible. If placed in water the same is true. Also, if the medium moves over time, and readers are available over that spatial range, additional information could be derived.

Still further, even emplacement in a medium such as manure would allow an easy way to probe that substance and gather measurements. This can be, if desired, spatially close to animals of interest as well as temporally close to the time creation of the manure if desired. It can be monitored over time if such information is deemed valuable.

Probing of small objects such as cells, such as is possible here, is not possible with many sensors.

FIG. 10 also indicates, at step 208, that once a measurement is taken and acquired, it can be taken again at a different time at the same medium. Alternatively, (e.g. step 209), the user could remove the sensor assembly and insert it again for another measurement, or into a different location or even different medium or sample if properly reconditioned.

C. Generalized Embodiment Focused on in Planta Sensing

At a generalized level, but particular to plant tissue sensing, the invention can include these aspects:
a. Access to relevant internal plant tissues with needled probe. A probe body which has a form factor that allows it to be inserted or implanted into plant tissue with minimal invasiveness. Ideally the minimum invasiveness has no material detrimental effect on plant health, growth, or development. For example, it does not remove or destroy substantial tissue or disrupt plant development functions. It does not materially block plant access to light or air for photosynthesis. It does not weigh down shoots or roots substantially. It does not disrupt the flow of fluids in the plant materially. As such, at least the portion of the probe that is inserted in the plant tissue is micronized. Like a small needle into human dermis, this microneedle form factor meets these objectives. It can be solid or hollow. It can carry a single sensor element or multiple sensor elements. It can be a single needle point, two side-by-side (e.g. FIGS. 20A-B), or even three or more parallel needle points from a substrate.
b. Transduction of Relevant Measurements from the Accessed Tissue. Sensing can be with electrode-based micro-sensing elements (one or more). This can be by use of electricity or by sensing electrical potential. Electrical power for these purposes can be on-board (e.g. battery, solar or wind), wired (e.g. from an external source), wireless from a remote source (e.g. inductive), or using energy harvesting devices based on different principles (e.g., piezoelectric, triboelectric, thermoelectric, or combined). The latter three options allow the elimination of having to have a battery or other electrical power source on-board the probe. This has beneficial implications not only as to cost, but also lower weight and smaller size of the probe. It also allows the circuits to be passive and inactive until activated to save power consumption and increase useful operational life.
c. Microfluidic techniques can promote access and measurement. One example is indirect sensor contact with plant fluid drawn to the sensor with microfluidics. Capture of measurements for further use. Communication of information from the probe to an on-board memory, a wired reader, a wireless reader, or a remote receiver similarly allows reduction in complexity, cost, and size at the probe. The latter technique allows a single central station to include the components for providing wireless power to one or many probes within an operating range of the station, as well as gather by data telemetry measurement information from one or many probes within range. This allows cost-effective and efficient operation of from one to many probes and monitoring the measurements from the same. The probes are minute and minimally invasive. The central station is wireless and can manage many probes.
d. Installation reliability. A variety of techniques can be use used to promote good mechanical mounting to plants.
e. Manufacturing techniques. By manufacturing techniques such as MEMS, the probe can be manufactured to such small scale, including in batch or semi-batch modes. This also helps economic practicality. Relatively inexpensive probes can be distributed and used at a variety of plant locations and/or a variety of different plants. The information from monitoring from these various sites can be very valuable. It allows insight into plant processes on plant-by-plant basis or set-of-plants basis. But it further allows derivation of important correlations between plant development relative to the measured nutrient or other plant constituent and such things as soil types, environmental conditions (e.g. temperature, moisture, dust, debris, etc.). This has wide implications for not only crop producers but plant scientists in the plant advancement experiments and breeding/genetic development.

FIGS. 11A and B diagrammatically illustrate some of the above aspects. As indicated in FIG. 11A, plural plants in a field 95 can each have one or more micro-needled probes 10 installed. Each probe 10 can be implanted into the plant xylem to access the xylem fluid (at plant stalk 91 or otherwise). One or more micronized sensor elements 14/16 can be on each microneedle. An output section 18 can contain the circuitry for electrically obtaining a measurement from each sensor and either store the measurement on-board, or communicate to a wired or wireless device, storage, or reader 20'.

FIG. 11A diagrammatically illustrates at 102 that the needled probe 10 can (a) be solid or hollow, (b) be single or plural needles, (c) have one or more sensors operatively mounted somewhere on the probe body (or direct or indirect access to plant tissue or constituents provided via the probe body to sensors mounted elsewhere), and (d) have some type of interface to capture the sensor measurements for further use, whether storage, partial or full processing on-board, or wired/wireless connection to other components local or remote. FIG. 11A also is intended to indicate that one or more probes 10 can be installed on an individual plant, and/or one or more probes 10 on plural plants. Certain embodiments further allow data capture from plural probes 10 at a centralized source (see, e.g., FIG. 11A) and can include power transmission to the probes for their operation.

FIG. 11B diagrammatically illustrates how using the microneedle can access the xylem of stalk 91 of plant 90. Doing so allows access to the xylem vessels, which carry and transport water-based solution throughout the plant. The solution fluid contains a variety of chemical or chemical properties of interest. Examples are nutrients, hormones, and pH. Thus, the embodiments of the invention solve the problem of access to relevant chemicals in a plant by use of microneedle(s) 13A or B to penetrate into the xylem and either directly contact the fluid in the xylem or indirectly take up the xylem fluid by capillary action.

FIGS. 11A and B illustrate how the embodiment solves the problem of minimal invasiveness. The micro form factor of the microneedle(s) does not materially disrupt the normal plant processes, growth, and development, even if left installed for long periods, including a whole growing season. The microneedles are sized and installed to maintain penetration of the xylem even as the plant grows in size without material disruption.

As will be appreciated, the embodiment's use of microneedles can be combined with microfluidic techniques to promote go access to the fluid. One example is use of hydrophilic coatings (commercially available) on the needle ends (see FIGS. 21A and B). Another is microfluidic features such as microvalves or even pumps (see FIGS. 19A-C).

The micronization of the sensing element(s) allows them to be carried on-board the microneedle(s). There can even be plural sensing elements per needle point without material disruption of the plant (see FIGS. 13C, 13D, 18A, 18B). Microfabrication techniques allow the various possible combinations to be made. For example, needle points can be made from silicon and function effectively which allows such things as microfluidic features and sensing elements to be fabricated into the needle. Even at such small scale, such microfabrication techniques can be used to produce at least many of the features of the embodiments. Other materials are, of course possible. For example, needle points could be made of glass, acrylic, or other materials. Micromachining techniques can produce needed form factors with some of these materials.

The following specific examples are several ways aspects of the generalized invention can be implemented.

D. Specific Embodiment 1 (Hollow Needle/Internal Plant Sensor(s))

By specific reference to FIGS. 12A-B one exemplary embodiment of a sensor 10A according to aspects of the invention will be described.

Features of this embodiment include:
1. Hollow microneedle 13B to indirectly access plant fluid.
2. Single sensing element 40 inside the needle lumen 30, here a three electrode ISFET with an ion-specific nanofabric 41 (specific to nitrates) on the center electrode 42. Operation of ISFETs in the context of an ion-specific sensor such as to sense nitrates, as one example, are well-known. The size of ISFETs can be miniaturized to the scale indicated here. One example of an ISFET for such sensing is described at U.S. Pat. No. 6,306,594 to Cozzette, incorporated by reference herein.
3. Microfluidic features including one-way check valve 31 to hold fluid at the sensing element 40 (and not allow it to pass to the proximal end of the needle 13B) and an appropriately designed distal orifice and interior microfluidic channel 30 to promote uptake of fluid from the plant 90 when inserted. Microfluidic circuits and flow-control components such as valves, ports, pumps, and the like, are well-developed and well-known to persons of skill. They can be fabricated to needed scale by well-known techniques. See, e.g., U.S. Pat. No. 6,790,599 to Madov, incorporated by reference herein.
4. A three-terminal connection 43/45/47 (FIG. 12B) to an output interface for receipt and input of power to the electrodes 42/44/46 and output of electrical readings from the electrodes for correlation to, in this example, nitrate concentration.
5. Installation to the plant 90 can be simply insertion of the microneedle 13B into the plant. Alternatively, the whole assembly could be taped, adhered, clipped, clamped or otherwise assisted in its mounting to the plant (see, e.g., FIGS. 16A-C).
6. Microfabrication techniques (e.g. MEMS) can be used to form the hollow microneedle out of silicon, as well as the microfluidic channel, one-way valve, and the interior sensing element.

This particular sensor 10A includes a micro-sized probe body (here inside the microneedle itself) (see FIG. 12A). An ion-specific sensor in the form of a nitrate sensing element 40, is inside the microneedle 13B along a microfluidic channel 30 from the distal needle end opening. The one-way check valve 31 (microfluidic) is built-into the channel 30.

The needle 13B accesses the plant tissue. Its small form factor allows the probe 13B to be manually pushed into plant tissue almost anywhere on a plant (see FIG. 12A). As will be appreciated, this includes shoots and stalks of a maize plant 90. The microneedle 13B allows penetration of even tough maize stalks. It also allows placement in the plant roots (e.g. by digging and exposing them).

Capillary action automatically feeds fluid from that plant tissue to the probe channel 30. (see FIG. 12A). The check value 31 is configured to close off the proximal side of the needle hollow 30 and promote uptake of plant fluid in one direction from the needle distal end to the sensing element 40. The check valve 31 therefore allows just a small volume of fluid to be removed from the plant (e.g. 10 µL). As will be appreciated by those skilled in the art, this small volume of plant fluid is continuously refreshed to the sensing element 40 over time by diffusion from natural movement of fluid in the plant and the access to that fluid by penetration of the needle to it. Because the needle 13B and channel 30 are micro-scale, the amount of plant fluid is negligible. Therefore, continuous movement into and out of needle distal end is not materially detrimental to plant health or development. There is no significant loss of plant fluid with the dimensions of the probe of this scale.

As indicated, the microneedle 13B can be accurately formed, even at this small scale, from silicon by MEMS techniques, as can the integrated one-way check valve 31 and placement of traces for the electrodes 42/44/46 of the sensing element. US:2002/0138049A1, incorporated by reference herein, includes descriptions relating to different materials, manufacturing techniques, and form factors for microneedles.

As further explained below, this example of a sensing element improves accuracy by modifying a conventional ISFET. A fibrous-mat 41 of nano-scale strands or fibers (see FIG. 12C) is mounted on the working electrode of the ISFET. The mat 41 is engineered to promote trapping of the ionic-species of interest. This promotes improved accuracy because the sensing element is presented a concentrated amount of those ions at its measuring location. This also improves accuracy by deterring accumulation of other ionic species at that measurement location (i.e. they tend not be trapped there). U.S. Pat. No. 6,306,594, cited above, describes the basic features and operation of an ISFET, incorporated by reference herein, including its use as an ion specific sensor. As can be appreciated, such ISFETs can be micronized and produced by MEMS techniques. Additionally, US patent publication 2017/0234820 to Lettow, incorporated by reference herein, describes the functionality and benefits of nanoparticle coatings such as coating 41. The designer can select from a wide variety of functionalizations of such nano materials.

Experimental results validate the approach. (see FIG. 12D). Below is further description of the embodiment of FIGS. 12A-B.

Nitrate Microneedle Sensors for In-Situ, Real-Time Monitoring of Plant-Soil Nitrogen Dynamics for Field Studies Background: Nitrogen (N) is one of the most essential nutrients for crops. Crop and soil N levels are influenced by many factors such as climate, environment, fertilizer application, and mineralization. Real-time, in-situ, and precise monitoring of N uptake, fixation and response of plants to these environmental factors is highly desirable, because it can not only help to determine an economical and environmental friendly way of fertilizer application, but also is scientifically critical to examine and understand the effects of soil and weather environments on plant phenotype and, in particular, the interaction between genotype and environment of different plant lines.

Spectral measurements with spectrophotometer or reflectometer have long been used to assess the N status of plants by tracking variations in optical signature of N element. These optical measurement approaches, however, are expensive and need visible light illumination on the work area of plants (e.g., leave), and thus, are inconvenient to be deployed at different parts of plant (e.g., roots, shoots, stems) for field applications. On the other hand, commercial ion-selective electrodes are inexpensive, but they often have relatively large footprint, low sensitivity, and poor specificity with almost no ion recognition functionality.

Therefore, the existing N sensing technologies could not meet the practical needs of in-situ, real-time monitoring of plant-soil N patterns and dynamics at large scale for field studies.

An objective of this embodiment 10A (FIGS. 12A-B) is to develop ion-selective microneedle sensors with high specificity and sensitivity, for in-situ probing of N level at different parts of plants, as well as in soils. The microneedle sensors are designed small enough to be inserted into plant vessels, tissues, and organs, will automatically extract liquids of plant through built-in microfluidic channels and check valves, and will specifically measure local nitrate concentration of liquids in a real-time manner. By inserting the microneedles into soil, the sensors will also measure soil N levels. This allows the ability to adequately describe the spatial distribution and temporal variation of N in the plant-soil system. We have previously demonstrated a highly sensitive dedicated electrochemical sensor that selectively measures nitrate ions [1] (see B. Britz, E. Ng, H. Jiang, Z. Xu, R. Kumar, and L. Dong, "Smart nitrate-selective electrochemical sensors with electrospun nanofibers modified microelectrode," IEEE International Conference on Systems, Man, and Cybernetics, San Diego, CA, Oct. 5-8, 2014 (Page 3419-3422; DOI: 10.1109/SMC.2014.6974457), which is incorporated by reference herein) and this work can be applied here as an example. A nitrate-selective electrode of the sensor 10A of FIGS. 12A-B is formed by modifying the working electrode of the sensor with a nanofibrous mat 41 made of conductive polypyrrole nanofibers. Nanopores complimentary to the size of the target ions are created in the surface of the nanofibers and serve as nitrate ion trapping sites. The porous structure of the nanofibers provides a large surface area of interacting with the analyte. It has demonstrated that the sensor has high sensitivity of 1.2 nA/µM and detection limit of 0.062±0.014 ppm for nitrate ions, with almost no interference from chloride, sulfate, phosphate and perchlorate.

The microneedle sensor 10A of FIGS. 12A-B will integrate the previous nitrate-selective nanofiber-based electrochemical sensing element, a microfluidic capillary channel, check valve, metal microelectrodes, and silicon hollow microneedles, through MEMS technologies. The hollow needle has the micrometer tip size. The needle nature of the sensor permits analysis to be performed in situ by penetrating plants at a point of particular interest. The needle is treated hydrophilic (FIGS. 21A and B at 150) to enable automatic extraction of fluids from the plant to the sensing element (not shown) inside the microfluidic channel. The three electrodes 42/44/46 transmit electrical signal from the sensing element 42 to the outside of the device for post-processing. Because these MEMS devices can be made using batch fabrication techniques similar to those used for integrated circuits, levels of reliability and sophistication can be implemented at a low cost.

FIG. 12A (a) Schematic of using microneedle-type N sensor network for in-situ, real-time monitoring of the plant-soil N dynamics in field. Small triangles represent the microneedle sensors 10A. (b) Structure of a microneedle sensor 10A. (c) Nitrate-selective nanofibers 41 used in a microfluidic electrochemical N sensor 10A. (d) Response of our previous N sensor to nitrate level (see Britz, et. al, 2014 cited below, incorporated by reference herein). (e) Scanning electron microscope image of a silicon hollow needle.

Reference: [1] B. Britz, E. Ng, H. Jiang, Z. Xu, R. Kumar, and L. Dong, "Smart nitrate-selective electrochemical sensors with electrospun nanofibers modified microelectrode," IEEE International Conference on Systems, Man, and Cybernetics, San Diego, CA, Oct. 5-8, 2014; Page 3419-3422; DOI: 10.1109/SMC.2014.6974457.

The following will be appreciated by those skilled in the art regarding this embodiment:

Sensing Elements. Microfabrication techniques can be used to produce such micro-circuits/elements. Britz, E. Ng, H. Jiang, Z. Xu, R. Kumar, and L. Dong, "Smart nitrate-selective electrochemical sensors with nanofibers modified microelectrode," IEEE International Conference on Systems, Man, and Cybernetics, San Diego, CA, Oct. 5-8, 2014; Page 3419-3422; DOI: 10.1109/SMC.2014.6974457). gives further details. U.S. Pat. No. 4,020,830, incorporated by reference herein, gives details about selective chemical sensitive FET transducers. US 2003/0209451A1, incorporated by reference herein, gives details about microfluidic ion-selective electrodes sensors which use capillary uptake into a microfluidic channel that include plural ion-selective microcircuit sensing elements, including how such combinations may be manufactured.

Manufacturing of the microneedle. Microfabrication techniques can produce microneedles of this type and scale. For further details, reference can be taken to US2002/0138049 A1, U.S. Pat. No. 9,291,284, and Iwashita and Mita, "Needle-type In-situ Plant Water Content Sensors with Polyethersulfone Membrane, TRANSDUCERS 2009, 1849-1852, Denver, CO Jun. 21-25, 2009 and Ober and Sharp, A Microsensor for Direct Measurement of $O_2$ Partial Pressure Within Plant Tissues, Journal of Experimental Botany, Vol. 47, No. 296, pp. 447-454, March 1996, each of which is incorporated by reference herein. US2002/0138049A1 gives details about manufacturing microneedles, including use of microfluidic channels and valving. U.S. Pat. No. 9,291,284 describes microfluidics including one-way valves and how they can be manufactured.

Wireless Power and Data Telemetry. U.S. Pat. No. 7,226,442B2 and US2008/0014897A1, each of which is incorporated by reference herein, give details about techniques and components to provide wireless power to microchip devices as well as receive data from them.

As will be appreciated with reference to FIGS. 12A and B, a micro-sized sensing element can be built-into, built on, or otherwise fabricated into a microneedle lumen. The electrode-based sensing element can be electrically connected to a circuit (e.g. on a PCB to which the microneedle is mounted. Appropriate operation of the circuit allows ion-specific sensing of medium that is drawn into the lumen of the microneedle. By techniques known in the art (see some of the incorporated by reference citations herein), the electrode-based sensor element and other components of sensor assembly 10A can be used to: (a) inconspicuously mount to or into a medium of interest (e.g. plant or other), (b) without material disruption of the medium, take measurements which can, by calibration, be correlated to presence and/or concentration of ionic species of interest, and (c) communicate those measurements or have them read out by other devices.

FIG. 12A shows that additions/enhancements are possible. One non-limited example is use of materials such as graphene or nanofibers or particles. As described in cited references herein, such can assist in capturing or otherwise improving the measurement results. Fabrication of the overall sensor assembly, including microneedles, can be by known microfabrication techniques. Validation of results has been made (see, e.g., nitrate graph in FIG. 12A).

As will be appreciated by those skilled in the art, variations on the specific embodiment of FIGS. 12A and B are, of course, possible. The placement, type, form, sensing mechanism, and configuration of the sensor element can vary, as can the form of the microneedle, circuit board, and electrical connections. The circuitry to take the measurements and put them in a form for use can vary according to need or desire. This includes other micro circuit elements including different active sensing elements than ISFETs.

E. Specific Embodiment 2 (Flat or Planar Needle/Sensor(s) on Surface for In Planta Sensing)

An additional example of a sensor according to aspects of the invention is illustrated in FIGS. 13A-E. It is similar to Specific Embodiment 1 in some ways. But it also has differences as will be apparent below.

Features of this Embodiment 50A Include:
1. A flat or planar microneedle 13A (does not need a hollow) to directly access plant tissues.
2. Multiple sensing elements (e.g. ISFETS 56(1), 56(2), 56(3), . . . ) along the needle surface(s), here is an ISFET with an ion specific membrane 68 coated on the surface of the gate 66 of an ISFET), or like sensor 10A of FIGS. 12A-B.
3. Microfluidic features can include a hydrophilic coating (FIGS. 21A and B) on the needle distal end to promote fluid contact with the sensing elements.
4. A multi-terminal printed circuit board 14 with connections to an output interface 59(1), 59(2), . . . 59(N) for receipt and input of power to the sensing element electrodes 65A and B and output of electrical readings from the electrodes for correlation to ionic species concentration.
5. Installation to the plant 90 can be simply insertion of the microneedle 13A into the plant. Alternatively, the whole assembly could be taped, adhered, clipped, clamped or otherwise assisted in its mounting to the plant. 6. Microfabrication techniques (e.g. MEMS) can be used to form the microneedle out of silicon, as well as the sensing elements.

Figure 13A:
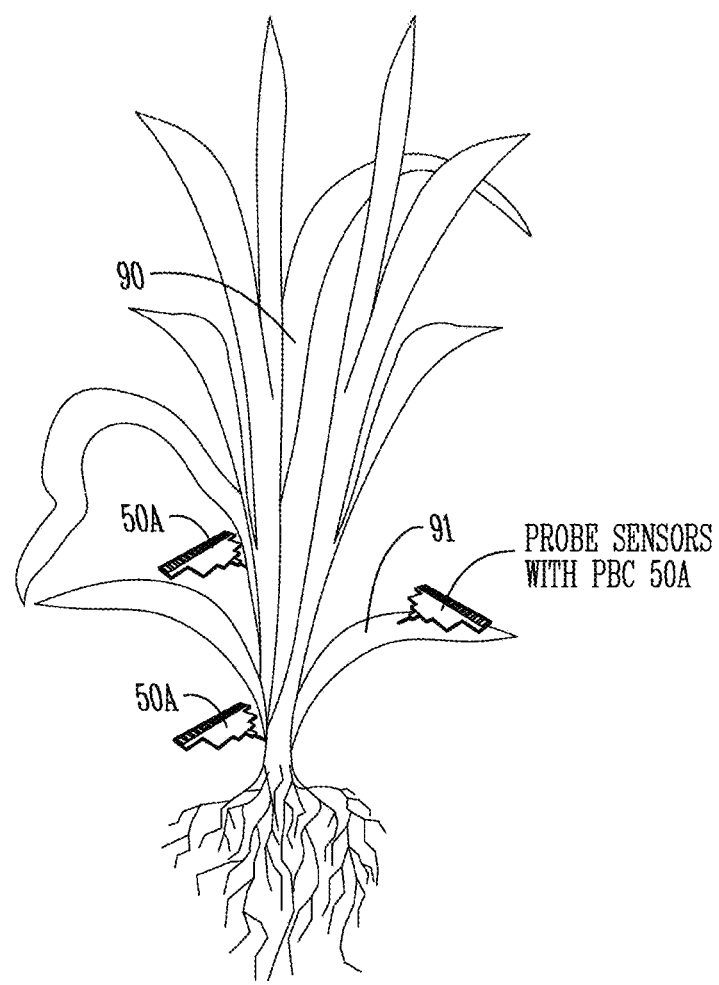
Figure 13B:
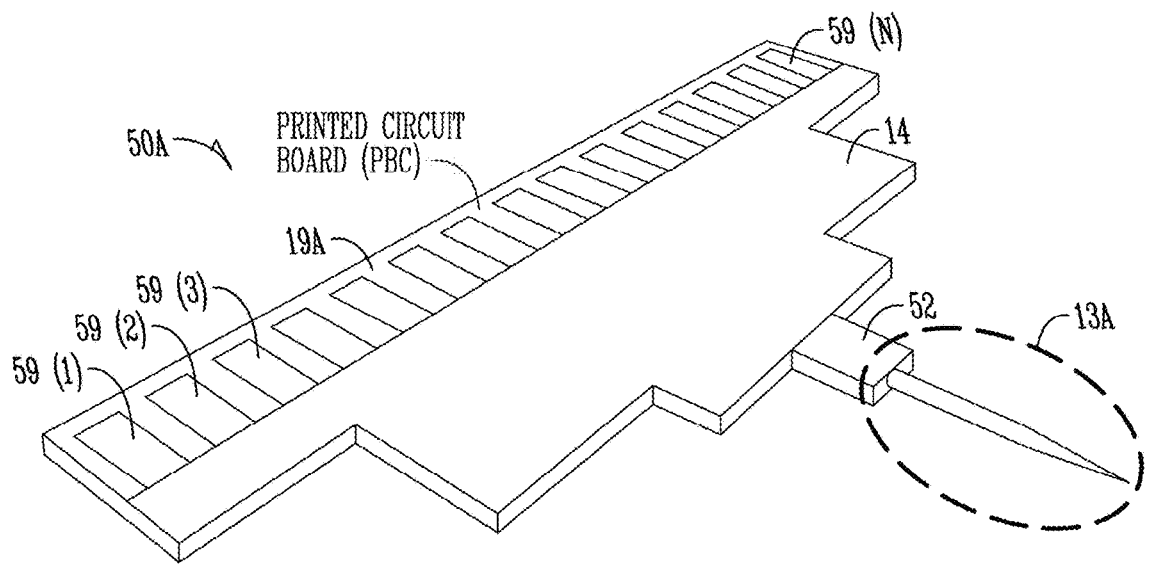
Figure 13C:
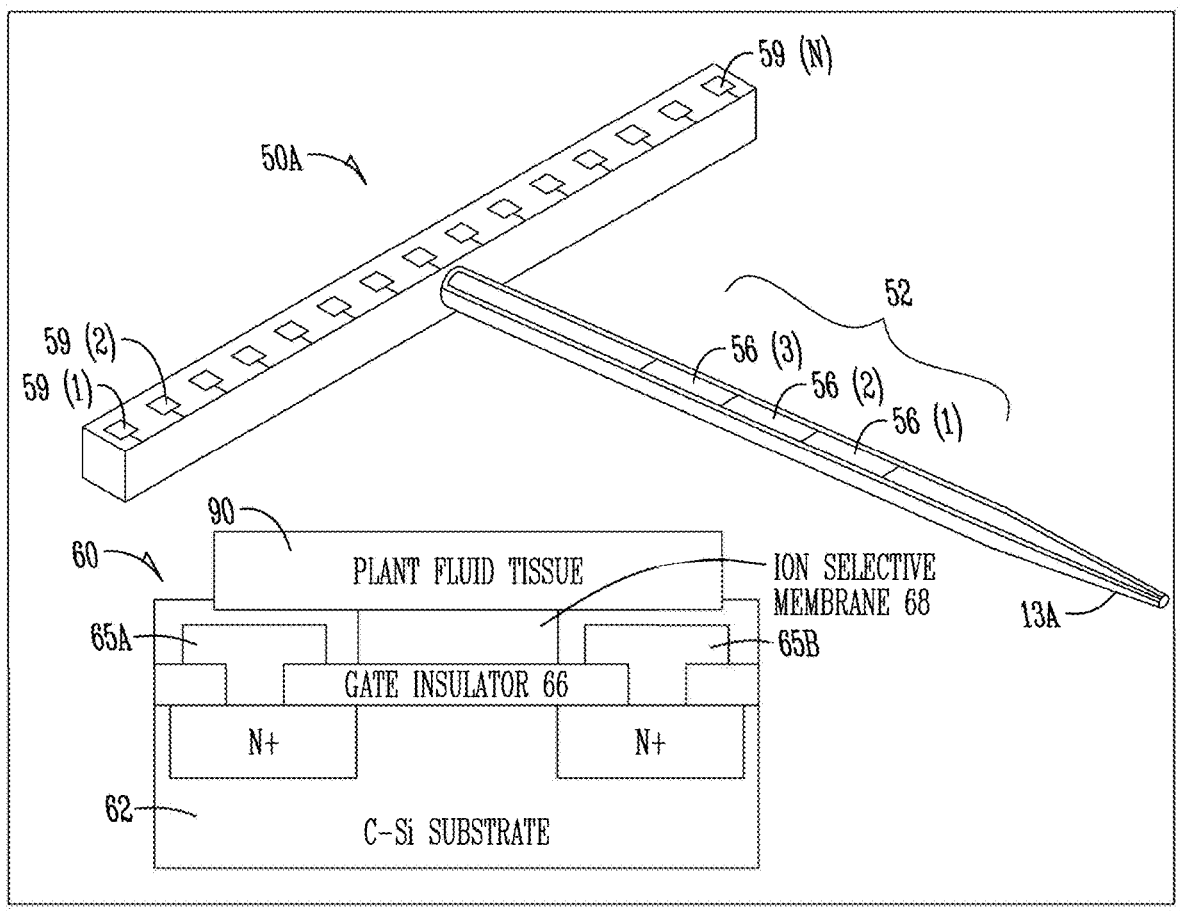

This embodiment uses a microneedle 13A (see FIGS. 13B and 13C). Note how it illustrates multiple sensing elements 56(1), 56(2) . . . (FIG. 13C) along the needle surface. This allows for simultaneous sensing for the same ionic species (such as for redundant measuring for improved accuracy) or sensing for different ionic species from the same probe (by configuring each sensing element appropriately; e.g. a different ion-specific coating).

Note also that the multiple sensing elements may require a larger interface (FIGS. 13B and 13C than that of the single sensing element version in FIGS. 12A and B. But as can be appreciated, such an interface to plural micro ISFETS can be on relatively thin, light weight circuit board substrate that would not be of a weight or size to detrimentally affect plant growth or development. Yet this embodiment allows plural sensing elements in one probe.

FIG. 13C illustrates in greatly enlarged diagrammatic form, an example of the modified ISFET, modified with the ion-trapping nano-fibrous mat 68, as discussed regarding Embodiment 1 above for a two-electrode sensing element. The mat collects/aggregates the ionic-species of interest (e.g. nitrate) right between the electrodes.

Figure 13D:
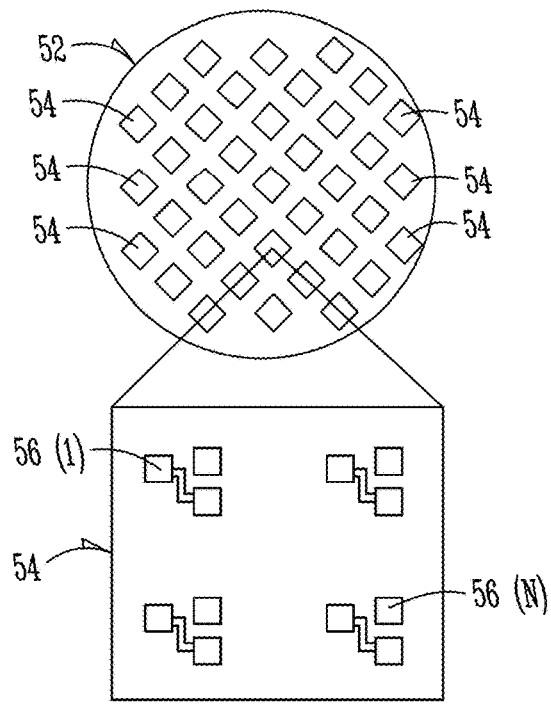

FIG. 13D assists in visualizing MEMS batch production of the ISFETS.

Figure 13E:
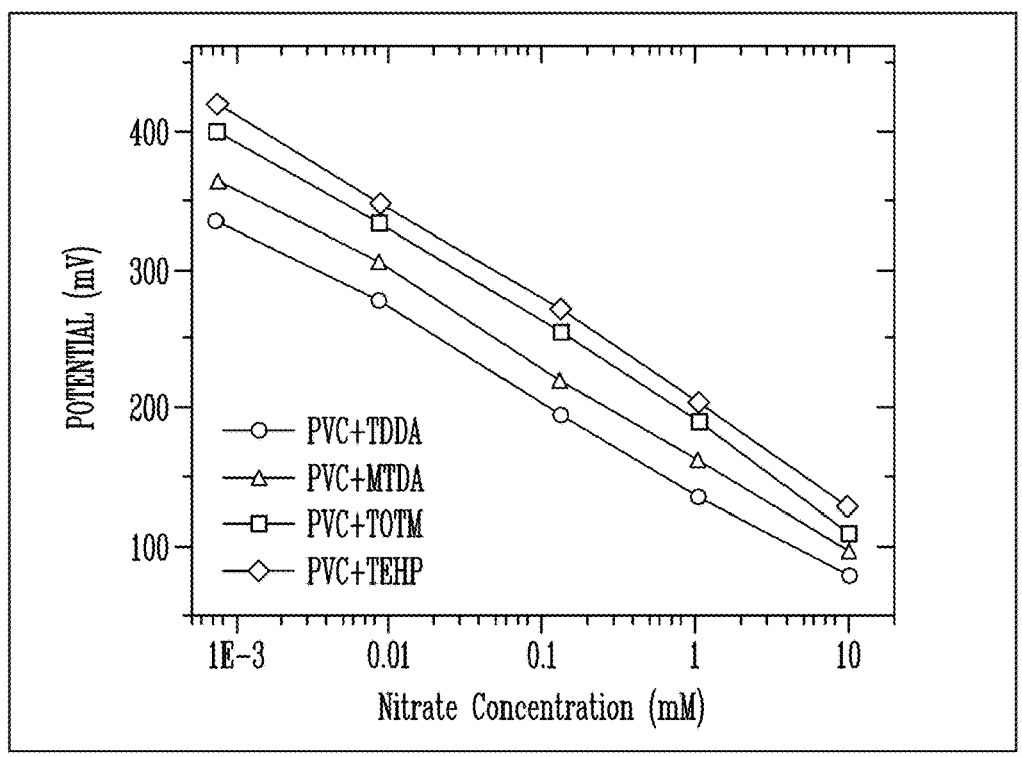

FIG. 13E illustrates proof of concept of this embodiment relative to nitrate for various configurations of the sensing elements.

Below is further description of the embodiment of FIGS. 13A-E.

The in planta 50A sensor disclosed here (FIGS. 13A-E) is made on a single crystalline silicon substrate 62 using micro-electro-mechanical systems (MEMS)-based micromachining techniques. The sensor is in form of a micromachined needle or probe 13A. The microprobe 13A can be inserted into the plant 90 at the different locations to monitor nutrient levels within the plant. Various sensing units, such as ISFET, enzyme FET, enzyme electrode, ion-selective electrode, electrochemical sensor, light-emitting FET, and quantum dot FET, can be miniaturized at the tip of the microneedle. A sensing unit 52 is responsible for the detection of a particular ion species in the plant through a specific sensing mechanism. Different sensing units or unit 56(1), 56(2), . . . , 56(N) can be used to monitor different ion species (nitrate, phosphate, sulfate, etc.). We have realized two-electrode based ion-selective sensing unit and three-electrode based ISFET sensing unit, at the tip of the microprobe sensor. The silicon-based semiconductor manufacturing technique allows for batch fabrication, thus offering low production costs.

Plant nitrate uptake. Plants have the ability to use either ammonium or nitrate as an inorganic N source. We are particularly interested in soil nitrate since its production is an indicator of the extent of nitrification and the potential for loss of N by leaching or denitrification. Root architecture, diurnal soil nitrate and ammonium concentrations, water availability, and the activities of transporters affect ammonium and nitrate uptake (140). Once nitrate is taken up by the root some is incorporated into root tissue while a substantial amount is transported into the shoot. Here we can examine nitrate uptake in roots and its translocation into shoots and how it varies by genotype and N-fertilization levels. Traditionally, these measurements have been restricted to only a few time points during growth because of the destructive nature of sampling. We overcome this limitation by developing the minimally invasive microprobe nitrate sensor capable of continuously monitoring plant nitrate levels in various types of roots (e.g., lateral or seminal) and the shoot, as described below. Furthermore, we couple these measurements with a sensor for continuous monitoring of soil nitrate levels at various distances (0, 2, 5, and greater) from the root. Placement of the sensors is a major issue, but because of their multiplex design we can place multiple sensors at different locations on the root or in soil. Importantly, the soil sensor can be placed in the same position in the soil as a root sensor (if used), enabling direct correlations between soil and plant nitrate levels. This technology can permit continuous nitrate measurements as the plant develops and the rhizosphere undergoes transitions from young to older roots. New sensors can be placed in emergent roots and adjacent rhizosphere soil. This can deliver detailed nitrate measurements at the soil-root interface.

Testing can be in microcosms on 20 genotypes under varying N-fertilization. Nitrate levels can be assessed shortly after emergence and continuously for the same length of time plants are grown. These datasets will provide an opportunity to evaluate correlations between N transformation rates, activity and taxa of N transformation genes, dominant microbial taxa, and soil and plant nitrate contents. Thus, this design permits assessing how genotype and N-input treatments influence these correlations.

FIGS. 13A-E. These figures further illustrate the following aspects of the design of sensors for measuring nitrates in plant tissues according to this embodiment. (a) multiple probes inserted into a plant, (b) mounting onto a PCB containing readout electronics, (c) sensor schematics with an inset showing the cross section of an ISFET sensor, (d) optical image of a silicon wafer with multiple ISFET sensors, and (e) the potential vs. nitrate concentration of 4 nitrate-specific ionophores tested in a poly(vinyl chloride) membrane.

A continuous microprobe nitrate sensor for measuring plant nitrate levels. The microprobe sensor 50A is based on the widely used ISFET capable of continuous sensing of various ions. One feature of sensor 50A is the minimally invasive, microscale needle 13A for insertion into the plant tissue 91 (FIG. 3). The high selectivity of probe 13A is achieved by depositing a nitrate-specific ionophore, such as methyltrioctylammonium nitrate (22), on a ion selective a poly(vinyl chloride) membrane 68 on the insulation material of the gate 66. At equilibrium, nitrate ions accumulating on the membrane 68 can cause a change in the potential, which is proportional to the concentration. These membranes 68 are highly sensitive and selective to nitrate ions (35). The optimal nitrate-specific ionophore can be identified by systematically evaluating their sensitivity, limit of detection, reproducibility, and response time, including in the presence of plant fluids and tissues to minimize interference by ions such as $Cl^-$, $NO_2^-$, $CO_3^{2-}$, $H_2PO_4^-$, and $SO_4^{2-}$. The device structure can be optimized in some situations by designing a holder to affix the microprobe sensor to the plant, an external readout circuit for the sensors. The result will be a highly sensitive and selective microprobe that can be inserted into plant tissues with minimal impact on the plant to provide continuous measurements of plant nitrate levels.

Again, those skilled in this technological field will appreciate that the needle, ISFETs, and other sensing elements and on-board circuitry for the probe can be made by MEMS techniques. Cost per probe can be kept relatively economical. But, also, variations or substitutions for one or more of the components can be made and provide analogous or needed functionalities.

FIGS. 13C, D, and E provide more details about use of ISFETs as the ion selecting sensing elements as well as how many can be fabricated in small form factor for use in this context of See, also, for example, U.S. Pat. No. 6,306,594 cited above, for details about ISFETs or variations in such sensing functions.

FIG. 13A diagrammatically indicates that such a sensor can be placed in different locations on a plant.

FIG. 14 gives additional information about the physiological structure of a maize plant and possible probe insertion and anchoring locations, including in the root system. This figure also indicates that sensors of the type of the given embodiments herein can be used in combination with other sensors. FIG. 14 gives a few examples. As is known in the art, a variety of measurements and information could likewise by correlated to on-plant sensed data. Examples include spatial, temporal, environmental, genetic, phenomic, soil type, fertilizer, insecticide, pathogen, or other information.

F. Specific Embodiment Three—Fabrication

As will be appreciated by those skilled in this technical field, MEMS type fabrication techniques allow creation of a variety of form factors and microfeatures in a fully or substantially integrated fashion in single device or body, or on a single substrate. Another possible embodiment utilizing aspects of the invention is illustrated diagrammatically at FIGS. 11A and B.

A single, integrated body could be fabricated out of silicon and include:
  a. A needle point section with one or more microsensors;
  b. On-board electronic processing circuitry section; and
  c. On-board output section, for example, an interface that handles both wireless power to the on-board circuitry and wireless reading of the sensor measurements.

Importantly, all these sections could be fabricated with MEMS techniques on or in a single or otherwise integrated silicon micro-sized needle body. This could be efficient and economical to manufacture and has a very small, stand-alone form factor. Similar to acupuncture needles, one or more of such small, self-contained integrated devices could be easily and minimally invasively placed almost anywhere on a plant, including a plurality of them placed in different locations on the same plant. There small size allows even quite close placement, but the circuitries and reading techniques could distinguish between them.

FIGS. 11A and B diagrammatically (not necessarily to scale) illustrate this concept. The needle body and one or more sensors per needle body could be any of the form factors of the other embodiments described herein. The electronic processing and output sections, including wireless power and data transfer, could function as described elsewhere herein but be micronized in size and integrated into the microneedle body.

G. Examples of Use of the Embodiments

Examples of possible uses of the probes/sensors of the disclosed embodiments are mentioned above. Others are possible. As appreciated by those skilled in this technical area, in planta (including in vivo) measurements of nutrients or other chemicals can inform a crop producer of valuable information during a growing season. It can inform of need to add fertilizer related to the measurement. It can also inform the grower further fertilizer is not necessary.

The measurements can also be used by the breeders to help understanding of how field conditions, crop genotype, and/or environment affect the crop growth when making decisions as to seed and inputs in future growing seasons.

The measurements can also be used by researchers. Armed with such in planta measurements, scientists gather valuable intelligence about how certain genotypes react to soil or environmental conditions (G×E interactions). And fertilizer, insecticide, herbicide scientists gather valuable intelligence about how the plants and the measured nutrient or other chemical(s) in it interact with fertilizers, insecticides, herbicides and the like.

As indicated above, with particular reference to FIGS. 2-7, the sensor assemblies 10 or 50, configured appropriately, can be used with non-plant mediums in analogous ways.

For example, sensors 10 embedded in soil can be equipped with wireless read-out and/or power supply. Optionally, a hydrophilic material can be added to at least part of the probe of the sensor. Those skilled in the art will appreciate variations to the micro sensors according to medium being investigated.

Other uses are, of course, possible.

H. Example of Wide-Area Distributed System of Sensors

FIG. 15A diagrammatically indicates a system according to aspects of the invention. The practicality and economies of sensors such as described above allows placement in a plurality of plants around a field. Measurements from many plants give enhanced information for producers or researchers. Variations of the measured chemicals in the plants spatially in the field can be beneficial.

As indicated above, part of the practicality of this combination is that a single central station 20 can service many probes in the field. It can supply wireless power and data telemetry to any probes within its range. The central station 20 can be configured to have sufficient range for at least as is indicated in FIG. 15A. Reference to U.S. Pat. No. 7,226,442B2 and US2008/0014897A1, each of which is incorporated by reference herein, give details about such wireless power and data telemetry systems, at least some of which can be applied in the present case.

As indicated below, at least for more widely-distributed sensors, it may be beneficial to have a directional antenna at the central power station that automatically rotates relative to the set of distributed probes. As indicated in U.S. Pat. No. 7,226,442B2 and US2008/0014897A1, there are techniques to sense when such a directional antenna is best aligned with a given probe. The system could utilize this to better ensure effective wireless power transmission to that probe and/or receipt of data from that probe. An omni-directional antenna is also possible if it has sufficient power and coverage for the area occupied by the set of distributed probes. Again, one of the features of this embodiment is that the probes do not have to carry on-board an electrical power source (e.g. battery). A centralized, dedicated wireless power transmitter can be used to power anywhere from one to many deployed sensors. The power transmitter consists of an inexpensive tower-mounted high-power transmitter and a directional antenna (see, e.g., FIG. 15A). The antenna can rotate, slowly scanning the area of deployment for the sensors. When the sensors come into the main beam, on-chip power harvesting circuitry can convert the radio-frequency or RF energy into DC power to power the sensor and the integrated wireless interface. The sensor can transmit its data back to the centralized data logging system and then power down. All sensors are completely batteryless and the output power of the centralized transmitter can be used to power hundreds of such sensors scattered across a large area of deployment. See U.S. Pat. No. 8,115,448 to John, incorporated by reference herein, for description of how this functions.

Two more non-limiting examples of how to remotely acquire measurement data of plant sensors 10 installed in a crop field follow, in addition to using a local central wireless station 20 that is already mentioned.

In FIG. 15B, a number of plant sensors 10 are installed in a crop field 95. Each plant sensor 10 or group of plant sensors 10(1), 10(2), . . . 10(N) use a wireless cellular module (not shown; installed in or on each sensor 10 and commercially available from a number of commercial sources add miniature size and relatively low power) to send measurement data and geolocation (i.e., GPS coordinates) of those plant sensors to the cloud network 180 using cellular network 181. A data receiving device 184 (e.g., cell phone, ipad, etc.) on the ground (e.g., home, office, or anywhere in the world as long as there is cellular or internet network access) can download the sensor measurement data and sensor location information. Sensor 10 measurement data is wirelessly sent in cellular communications 182 to cell network 181, which then communicates the data to the cloud 180. The cell communications 182 could also include GPS coordinates or geo-location information for each sensor 10 so its measurements can be correlated to specific field locations (e.g., via a GPS circuit on-board or at each sensor 10). Data from cloud 180 can then be selectively downloaded to one or more digital devices 184.

In FIG. 15C, a number of plant sensors 10(1), 10(2) . . . , 10(N) are installed in a crop field. Each plant sensor 10 uses a wireless Bluetooth module (not shown, installed in or on each sensor and commercially available from a number of sources, and miniature size and relatively low power) that can send measurement data a relatively short distance (e.g., within meters). A commercially-available drone carrying a data receiver with GPS (collectively ref. no. 190) can fly to above the plant sensors 10 to acquire measurement data. The drone-based data acquisition system 190 can be manipulated to fly over the field and wirelessly collect measurement data 192 (and, if configured, geo-location information) from each sensor 10.

FIG. 16D illustrates an alternative embodiment of a fully integrated device according to one embodiment of the invention. Miniature sensor 10' has essentially a housing 14' that functions both as a probe as well as self contains all other components needed for operation in that form factor. It can even include a probe end 13' that is in needle form. In one example, housing 14', with tip 13', can basically be a microneedle. As will be appreciated, and has been discussed herein, that case or housing 14' can be fabricated to include one or more sensing units 56(1), 56(2) . . . , 56(N) on board, on needle circuitry 16', wireless communication circuitry and components 18'. It can also include power/battery/energy harvesting unit 15' on board. All the functional units are directly manufactured on a single needle (e.g. silicon needle) that can be inserted and embedded into, for example, a plant, as a whole integrated device with all functional features in that single needle. As can be appreciated, there are different ways to fabricate or manufacture such integrated microsensors 10'. One is that the individual components shown in FIG. 16D could be manufactured separately and then assembled into a needle-like case. The case could be any of a variety of materials including but not limited to plastic, ceramic, etc. The assembled needle can be entirely inserted and embedded inside the material under investigation such as a plant or the other types of materials mentioned herein.

I. Options and Alternatives

As indicated above, the invention can take many forms and embodiments. Variations obvious to those skilled in this technical field will be included within the invention, which is not limited to the embodiments described herein.

Some additional discussion or and examples of options and alternatives follow.

1. Form Factor/Scale and Microneedle

The embodiments give indications of scale. Present MEMS and other manufacturing techniques allow micro and even nano scale production of these types of devices and functional components. The designer would balance the advantages of smaller scale with need functionality as well as with what is acceptable for minimal invasiveness with the plant involved. For example, a larger probe may be sufficient if placed in a maize stalk. Or a certain minimum diameter channel in the microneedle may be determined for the good capillary uptake of plant fluid.

MEMS techniques (e.g. semiconductor fabrication techniques) can fabricate the needle in conical form or with one or more flat sides with a range of taper angles. As indicated in the drawings, the needle point can be a fraction of the total length of the needle or the taper could be longer towards the proximal end. The microchannel in hollow needles could have uniform insider diameter or varying. Such techniques can be used to make fully or partially integrated sensor assemblies, including not only the needle(s) but at least some other components such as sensors, microcapillary features etc. As will be appreciated, however, the overall assembly could be made in other ways. It could have aspects made by semiconductor fabrication processes and materials and some by other micromanufacturing techniques.

Other materials are possible. One is glass for the needle (whether planar or hollow). Another is a hard polymer (e.g. acrylic or acrylic sheet) or ceramic. It is possible there is a combination of materials, for example, a needle point of glass and a proximal needle portion of polymer or silicon or ceramic.

Micromachining to form the needle or other parts is possible. US2002/0138049A1, incorporated by reference herein, describes some types of options and alternatives for microneedles in the context of penetrating human dermis. They include metals, ceramics, semiconductor material, organics, polymers, and composites. US2002/0138049A1—describes design parameters for microneedles including strength and form factor, as well as different ways to manufacture them with adequate precision. It describes hollow and solid, as wells as tapered, non-tapered, or combined tapered tip and straight-sided proximal portion. It discusses conical (circular-cross-section) tips as well as polygonal cross-section. It also building in such things as electrodes and microcapillary features.

The embodiments focus on a microneedle as the technique for insertion into plant tissue. There may be other forms of a probe tip that would also function.

Also, at the small scales involved, some embodiments might use a set of multiple microneedles on the same probe. FIGS. 17A-D diagrammatically illustrates a grid of parallel microneedle points 113 fabricated on a substrate. A sensor section 114/116/and/or 118 can be in communication with the needle points either via communication with a hollow microcapillary through each or otherwise with the needle point exteriors. The whole assembly 110 could be stuck on a plant 90 so that the needle points 113 penetration the epidermis to the xylem. As indicated different sensors elements 114/116 and/or 118 in the assembly could measure one or more things. Non-limiting examples are shown of different ionic species and hormones.

FIGS. 18A and B illustrate how each needle point could be solid (FIG. 18A) or hollow (FIG. 18B). Sensing elements (one or more) could be external (FIG. 18A) or internal (FIG. 18B).

FIGS. 20A and B illustrate another possible embodiment. Side-by-side needles (solid at 13A(1) and 13A(2) or hollow at 13B(1) and 13B(2) or a combination of one solid and one hollow) could be fabricated as an integrated unit. This could allow more surface area or space for sensor elements. It could also allow for improved mechanical qualities for the assembly (e.g. improved mechanical resistance to bending, breakage, or deformation when pushed into a plant). One needle could essentially be passive in the sense it is simply used as mechanical reinforcement and has not sensing functions.

2. Microfluidics

As indicated in some of the appendices, microfluidics allows a variety of fluid circuits at small scale. The designer may add additional microfluidic configurations or components according to need or desire.

For example, there may be additional flow control components. One might be a valve to hold fluid at the sensing elements in a hollow needle. Selection of dimensions of the microcapillary channel including distal orifice into the hollow needle can influence capillary uptake from the plant.

FIG. 19A shows a one-way valve 31 in hollow needle 13B, with enclosed space 30A and sensor 120, such as discussed above.

FIG. 19B illustrates a possible embodiment where a fixed volume chamber 30B at the distal end of the needle 13B might contain one or more sensors 120 and eliminate the need for a one-way check valve.

FIG. 19C illustrates an optional potential feature. By microfluidic fabrication and configuration, the microneedle assemblies could optionally supply infusion fluid or solutions to the plant 90. A source of infusion fluid 124 could communicate with a microfluidic pump 122 into chamber 30C. The one-way check valve 31 of FIG. 19A could be included to hold a plant fluid sample for sensing at the distal needle tip 13B. But the pump 122 could be configured to produce sufficient fluid pressure to open the one-way valve 31 and allow infusion fluid 124 to be pumped into the plant 90 at 120. Non-limiting examples of such fluid might include dyes and nutrients.

Techniques of making and using microfluidics can be found at US 2003/0209451A1 and—US2002/0138049A1 each of which is incorporated by reference herein.

It is also noted that techniques such as use of hydrophilic coatings can be used to influence fluids and the probe.

3. Sensors

The nano-fibrous ion-trapping mats are one modification or enhancement of ISFETs mentioned above. Others are possible. Some non-limiting examples are discussed earlier. The sensing electrode may be coated with an ion-specific enzyme to recognize a target ion. For example, nitrate reductase enzyme can be used to modify the electrode surface to make the electrode specifically sensitive to the enzyme. Extended gate ISFETs can add sensitivity and take advantage of the elongated probe. See, e.g., US 2006/0046375 to Chou et al, incorporated by reference herein. For example, the sensing electrode may be coated with ion-specific enzyme to recognize target ion. For example, nitrate reductase enzyme can be used to modify the electrode surface to make the electrode specifically sensitive to enzyme.

Other sensors are possible and can be built-into or on a microneedle. Some non-limiting examples are discussed earlier.

FIGS. 22A and B diagrammatically illustrate three and two electrode type sensor elements, including indications about how they could be fabricated and configured. These are by no means limiting to the possible sensor element configurations. At least for ion selective sensing, at least one electrode is preferably coated with a relevant sensitive material.

As will be appreciated by those skilled in this technical field, the designer can choose between variations depending on need or desire. Some examples follow.

The type of measurement can vary. The electrode-based sensor elements can have two or more electrodes. A coating or material that is sensitive to the analyte of interest can be used with at least one electrode. Different electrical properties can be measured (e.g. current, voltage, etc.). More discussion of this type of sensing can be found at U.S. Pat. No. 4,020,830 incorporated by reference herein.

As mentioned, placement of one or more sensors per microneedle can be varied. One or more can be at the tip. If access is given to the relevant plant tissue (e.g. through microfluidics), the sensors can be away from the tip. One or more can be inside a hollow needle. One or more can be on the exterior of solid or hollow needles. Surface mount techniques could be used. Integrated fabrication techniques could be used.

Two side-by-side (15 abutment 125) needle embodiments (e.g. FIGS. 20A and B) could place one electrode on one needle and the other electrode on the other needle. As indicated, the electrodes could be on one needle and the other needle used just for mechanical strength of the combination.

4. Wireless Interface

The circuitry needed on-board the sensor probes to facilitate reception of wireless power and transmission of measurement data is indicated at attached U.S. Pat. No. 7,226,442B2 and US2008/0014897A1, each incorporated by reference. The designer of the present system can make variations according to need or desire.

Wireless Station

Similarly, U.S. Pat. No. 7,226,442B2 and US2008/0014897A1 (both incorporated by reference herein) give ideas about how a central station could facilitate wireless power and data telemetry from distributed probes. The designer can make variations according to need or desire.

6. Manufacturing

Several techniques for fabricating the sensor components have been mentioned above. As will be appreciated by those skilled in the art, MEMS techniques, including semiconductor type fabrication techniques, have capabilities that provide certain potential benefits. But the invention is not necessarily limited to those techniques US2002/018049A1 has substantial description about some techniques applicable here.

As will be appreciated, aspects of the invention can be implemented through highly integrated, MEMS manufactured assemblies. Alternatively, a more modular technique might be used. For example, a glass needle could be assembled to a sensor module. A PCB (printed circuit board) could be operatively connected to the sensor module. Various combinations and alternatives are, of course, possible. Iwashita and Mita, "Needle-type In-situ Plant Water Content Sensors with Polyethersulfone Membrane, TRANSDUCERS 2009, 1849-1852, Denver, CO Jun. 21-25, 2009, and Ober and Sharp, A Microsensor for Direct Measurement of $O_2$ Partial Pressure Within Plant Tissues, Journal of Experimental Botany, Vol. 47, No. 296, pp. 447-454, March 1996, each incorporated by reference herein discuss probe manufacturing and assembly in different contexts but certain of those concepts can be applied here.

7. Installation/Placement

Techniques of mounting the different embodiments to plants have been discussed above. So also have the variety of positions on a plant these embodiments might be inserted or emplaced, including plural probes at spaced apart positions on a plant.

As will be appreciated, other techniques can be used to improve the adherence, robustness, or other operating features of the sensor assemblies once in place on the plant.

For example, FIGS. 21A and B illustrates how one technique to improve fluid uptake is coating at least the distal needle end with hydrophilic material. Another example is to essentially pot (see 152) at least the proximal end of the assembly (e.g. in epoxy or the like) to seal it and at least some of the electrical components or surfaces from moisture, dust, debris, or the like.

Alternatives include using spring clips to help hold the sensing assembly 10 to the plant. See, e.g., FIGS. 16A-C. It is releasable as a holder. FIG. 16A shows a body 80A with concave surface to abut the generally convex surface of a plant stalk 91 and support the readout circuit and signal processor 81A. It also holds the needle(s) in place at the stalk by a ring clamp 82A of flexible but resilient material to constantly urge the ring claim against the plant stalk but allow the ring clamp to expand (at least over a reasonable range) with growth of the stalk circumference over time by adjusting fastener 83. See also, U.S. Pat. No. 2,689,141 to Kiekhaefer, incorporated by reference herein. FIG. 16B shows two-plate 84T and B clamps and fasteners 85 installable across a leaf 92 to hold the needle(s) in place and support the proximal circuit board 81B in housing 80B. The clamp 84T/B also allows leaf growth because the leaf would tend to principally grow laterally in width and there is lateral room in the clamp for this.

As will be appreciated, these types of clamps, and other possible installation structures, could be made of light weight but reasonable durable materials for their functions and environment. One example is plastic, including plastic that would not substantially expand under typical higher outdoors temperatures.

Another example is to apply a light flexible polymer or foam layer over at least part of the assembly to protect to exposed part of the assembly. Glue or epoxy could then be added over the foam. This could also improve mechanical strength and seal those portions.

FIG. 16C shows a still further embodiment. Needle 13 with its circuit board 14/16/and/or 18 with electrical leads 19 could simply be sandwiched between two thin foam pieces 86L and R. They are available from 3M, St. Paul, Minnesota under product number MFR #: 4056. They have adhesive 88L and 88R. Positioning needle 13 and circuit board 14 as shown in FIG. 16C allows convergence of the two foam plates 86L and R to encapsulate portions of needle 13 as well as the whole circuit 14 into the form indicated. It is a light weight, cheap way to seal in the circuit with the distal end of needle 13 exposed for insertion on stalk 91. The foam is substantially mechanically strong, hydrophobic, low cost and robust (even for harsh outdoor environments) and includes built-in adhesive to connect them.

J. Alternative Sensing Circuitry

FIGS. 22A and B, and 23A-C illustrate several different ISFET embodiments that could be used with embodiments of the invention.

As previously mentioned, FIGS. 22A and B show different ISFET configurations. FIG. 22A has circuit 130 with channel 132 supporting source 134A and drain 134B. The gate insulator 136 spans the source and drain (i.e. channel). Insulators 135A and 135B bracket reference electrode 138. The circuit can be used to sense the electrolyte or analyte 121 or 123.

Figure 22B:
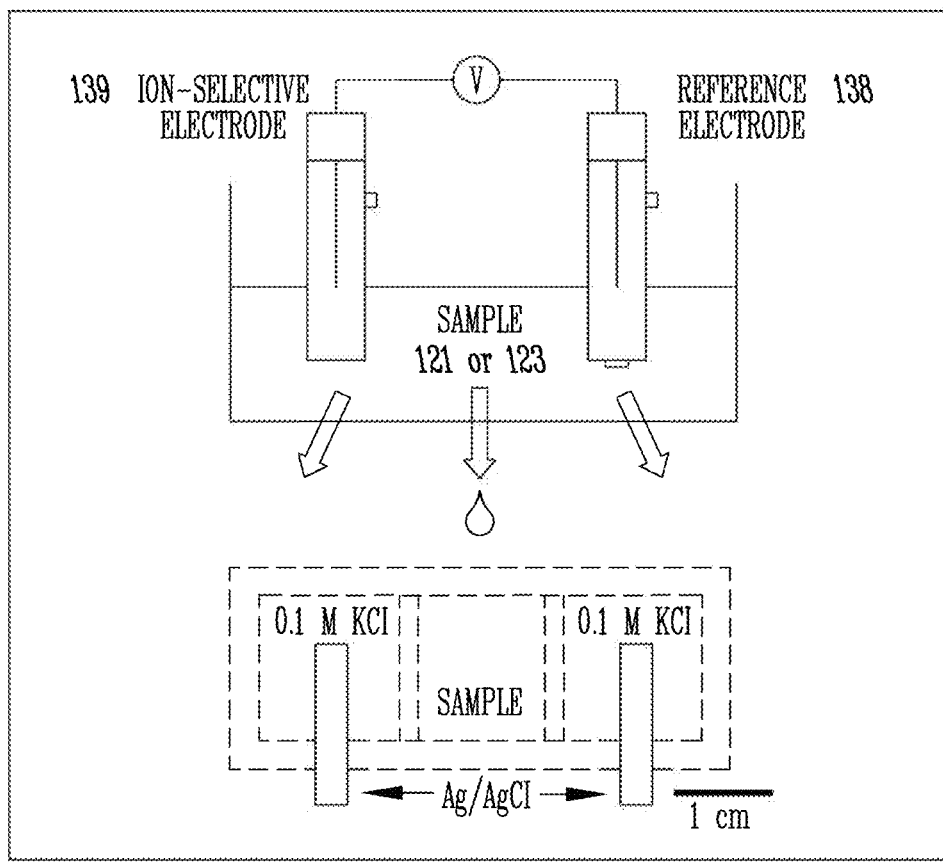

FIG. 22B shows a two electrode ion selective setup having reference electrode 138 and ion selective electrode 139 for the analyte sample 121 or 123.

FIG. 23A shows what is called an extended gate ISFET. As can be seen, the extended gate 137 allows extension of the ISFET along the probe 13. In other words, the whole needle serves as a sensitive gate of the ISFET. This can be beneficial with regard to improved sensitivity due to the increased sensing area. The sensor 130B includes the substrate 132, the gate insulator and the extended gate 137. See, e.g., US 2006/0046375 (incorporated by reference herein) to Chou for description of extended gate ISFETS.

FIG. 23B diagrammatically illustrate the probe end with the extended gate can take various form factors (e.g. form factors 13A-E). Additionally, FIG. 23C shows that coatings such as sensitive coatings 131 can be added along the probe.

A discussion of ISFET with extended gates can be seen at US patent publication 2006/0046375.

FIG. 24 illustrates another optional feature according to the invention. The ability to add additional active components to the miniature sensor assembly 130B is possible. FIG. 24 shows, for example, a serpentine antenna 162 can be fabricated on tip 13 and connected to board assembly 18. As discussed, it can be used as a wireless transmission communication module component 18 antenna.

FIG. 24 shows another subtle but advantageous aspect optional with the sensor assembly. In this assembly 130B, a temperature sensor 164 is fabricated on the needle 13 to detect temperature in a plant. It can be in communication with the measurement circuitry 16 used for the probe. It can be beneficial to concurrently or at least when desired also gain temperature measurements at the assembly 130B. Temperature sensor 164 can be any microcircuit temperature sensor including thermocouples and thermistors. US patent publication 2007/0194913 to Yokoshima and U.S. Pat. No. 7,830,228 to Brown, each incorporated by reference, describes how they would be manufactured and used.

FIGS. 25A-C show a still further optional implementation 170 of aspects of the invention. Instead of utilizing probe 13F to either move fluid and/or support electrically based sensing elements, probe 13F of FIG. 25A is essentially a wave guide. The probe body of 13F itself could be the fiber-optic or the like. Alternatively, it could be a different material but support longitudinally a fiber-optic from an optical detection circuit 16F to its distal end which would be an optical interface 172. Insertion of that distal end into the medium and operation of the optical detection circuit 16F would allow light to be directed to the interface 172. As is well known in the art, return light to the detection circuit can be evaluated. Any offset of returned light from that that was transmitted can be calibrated to a measurement of some characteristic at the optical interface 172.

Calibration can correlate return light detected from the interface between the waveguide and the medium under investigation (e.g. plant tissue 91). Different techniques/mechanisms can be utilized or added to the waveguide for different optical sensing effects, including various optical resonance. See, e.g., U.S. Pat. No. 6,303,386 to Klimart, incorporated by reference herein.

There are a variety of optical sensing techniques that are applicable, such as various types of optical resonators (e.g., photonic crystal, surface plasmon resonance, whispery gallery mode, grating, etc.) See U.S. Pat. No. 5,627,922 to Kopelman, for some examples, incorporated by reference herein. It is to furthermore be understood that various functionalized surfaces, coatings, or devices can be placed at optical interface 172 for various benefits such as are known in the art.

FIG. 26 is a flow chart of an optional methodology of use of an in planta needle based sensor. Method 200B is similar to method 200 of FIG. 10 with the following differences. A microneedle-based plant sensor is installed to the plant by stabbing the microneedle into the plant (step 202). The measurement can then be taken (step 204). That measurement can be stored, converted, processed, or communicated (step 206).

An optional utilization could be that once one or more measurements are taken in steps 202, 204, and 206, for a plant or a specific plant location, the small sensor assembly can be removed from the plant (step 210). With easy and minimal reconditioning (e.g. cleaning, rinsing, and perhaps sterilizing), (step 212), the sensor can then be stabbed into a plant and measurements taken. In particular, this obviously allows repositioning in a different part of the same plant or into a different plant. The reconditioning is simply to purge the plant contacting portions from contamination for the next measurement cycle. Any number of reconditioning techniques can be used according to need or desire. Non-limiting examples include washing, wiping, flushing, etc. with towels, sponges, fluids, gases, etc. In one example, multiple re-uses are possible (e.g. at least a dozen).

1. Applications

Examples have been discussed above. Again, sensed parameters with electrode-based sensing elements can include:
 a. Ionic species
 b. Nutrients
 c. Glucose
 d. Hormones
 e. pH
 f. Enzymes
 g. Pesticides
 h. Bacteria
 i. Fungi
 j. Temperature As mentioned, sensing measurements with the above-embodiments can be used in combination with other measurements by other measuring tools or sensors. The results of all these measurements can be analyzed and correlated.

Further examples are as follows:
 k. Toxins
 l. DNA or other proteins
 m. Biomolecules As will be understood by those skilled in the art, the microsensors and micro-sensing techniques discussed herein can be utilized with a wide range of sensing elements and techniques for a wide range of mediums of interest (analytes). The analytes can include, but are not limited to, animal and human skin or tissue, microorganisms, cells, enzymes, antibodies, nucleic acids, or materials or components that bind to the foregoing. The sensing element(s) of the microsensor(s) discussed herein have some type of detector or transducer which transforms one signal into another one in any of various ways. Non-limiting examples are optical, electrical, electrochemical, resulting from the interaction of the analyte with the detector or transducer to result in a measurement or quantification.

A reader with associated electronics or signal processors can convert the measurement or quantification to a form desired by the user.

The embodiments of the invention incorporate sensing elements for different analytes and analyte parameters into a low-cost, micro-scale, integrated assembly for emplacement unobtrusively at the location of the analyte, including in plant, in vivo, or otherwise.

What is claimed is:

1. A method for sensing an ion analyte in a sample, said method comprising:
 providing an integrated miniature sensor assembly comprising a microneedle operably connected to a sensing element comprising an electrode and an ion-selective material;
 contacting the microneedle to a sample;
 transducing a measurement describing an amount or concentration of an ion analyte in the sample by measuring a change in an electrical property of the sensing element.

2. The method of claim 1, wherein said sample comprises a plant tissue, a plant cell, and/or a plant fluid.

3. The method of claim 1, wherein said sample comprises manure and/or soil.

4. The method of claim 1, wherein said sample comprises water.

5. The method of claim 1, wherein said sample comprises agricultural tile water and/or overland runoff from crop areas.

6. The method of claim 1, wherein the sample has a volume of less than approximately 10 µl.

7. The method of claim 1, wherein the microneedle has a tip diameter of less than approximately 5 µm.

8. The method of claim 1, wherein contacting the microneedle to the sample comprises inserting the microneedle into a plant nondestructively for in planta or in vivo sampling.

9. The method of claim 2, wherein:
 said plant fluid comprises xylem fluid and/or phloem fluid; and/or
 said plant tissue comprises tissue from a root, shoot, stalk, leaf, grain, or seed.

10. The method of claim 1, wherein the electrical property is current, potential, and/or resistance.

11. The method of claim 1, wherein the analyte is an ion comprising nitrogen, potassium, phosphorous, and/or sulfur.

12. The method of claim 1, wherein the analyte is an ion comprising nitrogen.

13. The method of claim 1, wherein the analyte is nitrate or ammonium.

14. The method of claim 1, wherein said integrated miniature sensor assembly comprises a plurality of microneedles and a plurality of sensing elements and each microneedle of said plurality of microneedles is operably connected to a sensing element of said plurality of sensing elements.

15. The method of claim 13, wherein each sensing element of said plurality of sensing elements is responsive to a different analyte.

16. The method of claim 1, comprising transducing a plurality of measurements describing an amount or concentration of the analyte in the plant tissue or plant fluid during a time period of fractions of seconds, seconds, minutes, hours, days, weeks, or months.

17. An integrated miniature sensor assembly comprising:
 a microneedle subassembly operably connected to a sensing element subassembly and configured for nondestructive and minimally invasive in vivo or in situ access to an accessed medium or sample, the microneedle subassembly comprising one or more microneedles, the sensing element subassembly comprising one or more sensing elements,
 wherein at least one of the sensing elements comprises an electrode and the electrode is modified with an ion-specific material configured to trap and take one or more measurements of an ionic species related to the ion-specific material in an accessed medium or sample; and
 an on-board interface operatively connected to the one or more sensing elements and adapted to communicate the one or more measurements to a measurement circuit.

18. The integrated miniature sensor assembly of claim 17, wherein the ion-specific material is a membrane, nanofabric, or nanofibrous mat or a coating.

19. The integrated miniature sensor assembly of claim 17, wherein at least one of the one or more microneedles has a volume of less than approximately 10 µl and/or wherein the at least one microneedle has a tip diameter of less than approximately 5 µm.

20. The integrated miniature sensor assembly of claim 17, wherein the ion-specific material comprises trapping sites that trap an ion comprising nitrogen, potassium, phosphorous, and/or sulfur at the electrode surface.

21. The integrated miniature sensor assembly of claim 17, wherein:
- said one or more microneedles comprises a plurality of microneedles and said one or more sensing elements comprises a plurality of sensing elements;
- each microneedle of said plurality of microneedles is operably connected to a sensing element of said plurality of sensing elements; and
- each sensing element of said plurality of sensing elements is responsive to a different ion analyte.

22. The integrated miniature sensor assembly of claim 17, wherein:
- said one or more microneedles comprises a plurality of microneedles and said one or more sensing elements comprises a plurality of sensing elements;
- each microneedle of said plurality of microneedles is operably connected to a sensing element of said plurality of sensing elements; and
- at least two sensing elements of said plurality of sensing elements is responsive to a same ion analyte.

23. The integrated miniature sensor assembly of claim 17 wherein the in vivo or in situ access comprises minimally invasive access to the medium or sample of interest with the one or more microneedles, at least one of the microneedles comprising a single solid microneedle with at least one of the one or more sensing elements on the solid microneedle.

24. The integrated miniature sensor assembly of claim 17 wherein the in vivo or in situ access comprises minimally invasive access to the medium or sample of interest with the one of the one or more microneedles, at least one of the one or more microneedles comprising a microneedle with a hollow interior with a microcapillary scale channel along which are at least one of the one or more sensing elements, wherein the one or more sensing elements comprise one or more micro-sized sensors.

25. The integrated miniature sensor assembly of claim 17 wherein the at least one of the one or more sensing elements comprises:
  a. at least two electrodes.

26. The integrated miniature sensor assembly of claim 17 wherein the measurement circuit is configured to derive ionic-species-specific estimates for the accessed medium or sample of interest.

27. The integrated miniature sensor assembly of claim 26 wherein the ionic-species-specific estimates relate to at least one nutrient level in a plant tissue at each of one or more measurement times for the one or more measurements.

28. The integrated miniature sensor assembly of claim 27 wherein the nutrient level is nitrogen level based on nitrate concentration.

29. The integrated miniature sensor assembly of claim 17 further comprising a plurality of said integrated miniature sensor assemblies in operative connection to a central station.

30. The integrated miniature sensor assembly of claim 17 wherein the medium or sample of interest comprises:
  a. plant tissue;
  b. human tissue;
  c. fluid;
  d. particulate matter;
  e. a cell; or
  f. manure.

31. The integrated miniature sensor assembly of claim 17 further comprising an additional component on or near the one or more microneedles or the one or more sensing elements.

32. The integrated miniature sensor assembly of claim 31 wherein the additional component comprises one of:
  a. an antenna; and
  b. a temperature sensor.

* * * * *